US010679516B2

(12) United States Patent
Darmour et al.

(10) Patent No.: US 10,679,516 B2
(45) Date of Patent: Jun. 9, 2020

(54) CRAVING INPUT AND SUPPORT SYSTEM

(71) Applicant: Morningside Venture Investments Limited, Newton Centre, MA (US)

(72) Inventors: Jennifer A. Darmour, Seattle, WA (US); Jenny E. Hapgood, Tacoma, WA (US); David Evans Roth, Issaquah, WA (US); Ronald A. Overbeck, Winthrop, WA (US); Alan Joel Levy, Bellevue, WA (US)

(73) Assignee: Morningside Venture Investments Limited, Newton Centre, MA (US)

( * ) Notice: Subject to any disclaimer, the term of this patent is extended or adjusted under 35 U.S.C. 154(b) by 66 days.

(21) Appl. No.: 15/551,178

(22) PCT Filed: Mar. 11, 2016

(86) PCT No.: PCT/US2016/022117
§ 371 (c)(1),
(2) Date: Aug. 15, 2017

(87) PCT Pub. No.: WO2016/145373
PCT Pub. Date: Sep. 15, 2016

(65) Prior Publication Data
US 2018/0033330 A1 Feb. 1, 2018

Related U.S. Application Data

(60) Provisional application No. 62/132,436, filed on Mar. 12, 2015.

(51) Int. Cl.
*A61B 5/00* (2006.01)
*G09B 19/00* (2006.01)
(Continued)

(52) U.S. Cl.
CPC ............ *G09B 19/00* (2013.01); *A61B 5/0205* (2013.01); *A61B 5/02055* (2013.01);
(Continued)

(58) Field of Classification Search
CPC .......... A61B 5/00; A61B 5/015; A61B 5/6804
See application file for complete search history.

(56) References Cited

U.S. PATENT DOCUMENTS 2,183,482 A 12/1939 Kurkjian
3,279,653 A 10/1966 Pfleger
(Continued)

FOREIGN PATENT DOCUMENTS

AU 662877 B 9/1995
BE 899037 A 6/1984
(Continued)

OTHER PUBLICATIONS

Darmour et al.; U.S. Appl. No. 16/115,415 entitled "Craving input and support system," filed Aug. 28, 2018.
(Continued)

*Primary Examiner* — Omkar A Deodhar
(74) *Attorney, Agent, or Firm* — Shay Glenn LLP

(57) ABSTRACT

A craving control device comprising a housing, a craving input actuator supported by the housing, a wireless communicator supported by the housing, and a controller is provided. The craving input actuator can be configured to obtain information from a user pertaining to a timing, frequency, or intensity of a craving. The controller can be operatively connected to the craving input actuator and the wireless communicator to communicate craving information received by the craving input actuator via the wireless communicator to a device external to the housing. The device external to the housing can be a personal communication device. The housing can be sized and configured to be
(Continued)

enclosed in the user's hand and or to be placed in a pocket of the user's clothing. Methods for using the craving control devices are also provided.

37 Claims, 20 Drawing Sheets

(51) Int. Cl.
| | |
|---|---|
| *G06Q 10/10* | (2012.01) |
| *A61B 5/0205* | (2006.01) |
| *G16H 40/63* | (2018.01) |
| *A61B 5/0402* | (2006.01) |
| *A61B 5/0488* | (2006.01) |
| *A61B 5/11* | (2006.01) |
| *A61B 5/16* | (2006.01) |
| *G09B 5/02* | (2006.01) |
| *A61B 5/021* | (2006.01) |
| *A61B 5/024* | (2006.01) |
| *A61B 5/053* | (2006.01) |
| *A61B 5/08* | (2006.01) |

(52) U.S. Cl.
CPC .......... *A61B 5/0402* (2013.01); *A61B 5/0488* (2013.01); *A61B 5/11* (2013.01); *A61B 5/165* (2013.01); *A61B 5/486* (2013.01); *A61B 5/7455* (2013.01); *G06Q 10/10* (2013.01); *G09B 5/02* (2013.01); *G16H 40/63* (2018.01); *A61B 5/021* (2013.01); *A61B 5/024* (2013.01); *A61B 5/0533* (2013.01); *A61B 5/082* (2013.01); *A61B 2560/0242* (2013.01); *A61B 2560/0425* (2013.01); *A61B 2562/0219* (2013.01)

(56) References Cited

U.S. PATENT DOCUMENTS

| | | |
|---|---|---|
| 3,845,217 A | 10/1974 | Ferno et al. |
| 4,321,387 A | 3/1982 | Chavdarian et al. |
| 4,327,725 A | 5/1982 | Cortese et al. |
| 4,332,945 A | 6/1982 | Edwards |
| 4,379,454 A | 4/1983 | Campbell et al. |
| 4,545,990 A | 10/1985 | Le Foyer de Costil et al. |
| 4,579,858 A | 4/1986 | Ferno et al. |
| 4,590,278 A | 5/1986 | Edwards |
| 4,708,716 A | 11/1987 | Sibalis |
| 4,772,263 A | 9/1988 | Dorman et al. |
| 4,806,356 A | 2/1989 | Shaw |
| 4,853,854 A | 8/1989 | Behar et al. |
| 4,885,154 A | 12/1989 | Cormier et al. |
| 4,908,213 A | 3/1990 | Govil et al. |
| 4,917,676 A | 4/1990 | Heiber et al. |
| 4,917,895 A | 4/1990 | Lee et al. |
| 4,920,989 A | 5/1990 | Rose et al. |
| 4,952,928 A | 8/1990 | Carroll et al. |
| 4,953,572 A | 9/1990 | Rose et al. |
| 5,000,956 A | 3/1991 | Amkraut et al. |
| 5,013,293 A | 5/1991 | Sibalis |
| 5,049,387 A | 9/1991 | Amkraut |
| 5,069,904 A | 12/1991 | Masterson |
| 5,097,834 A | 3/1992 | Skrabal |
| 5,120,545 A | 6/1992 | Ledger et al. |
| 5,130,139 A | 7/1992 | Cormier et al. |
| 5,149,538 A | 9/1992 | Granger et al. |
| 5,149,719 A | 9/1992 | Ferber et al. |
| 5,212,188 A | 5/1993 | Caldwell et al. |
| 5,221,254 A | 6/1993 | Phipps |
| 5,227,391 A | 7/1993 | Caldwell et al. |
| 5,232,704 A | 8/1993 | Franz et al. |
| 5,232,933 A | 8/1993 | Lippiello et al. |
| 5,236,714 A | 8/1993 | Lee et al. |
| 5,242,934 A | 9/1993 | Lippiello et al. |
| 5,242,935 A | 9/1993 | Lippiello et al. |
| 5,242,941 A | 9/1993 | Lewy et al. |
| 5,248,690 A | 9/1993 | Caldwel et al. |
| 5,252,604 A | 10/1993 | Nagy et al. |
| 5,262,165 A | 11/1993 | Govil et al. |
| 5,273,755 A | 12/1993 | Venkatraman et al. |
| 5,273,756 A | 12/1993 | Fallon et al. |
| 5,304,739 A | 4/1994 | Klug et al. |
| 5,352,456 A | 10/1994 | Fallon et al. |
| 5,364,630 A | 11/1994 | Osborne et al. |
| 5,370,635 A | 12/1994 | Strausak et al. |
| 5,388,571 A | 2/1995 | Roberts et al. |
| 5,389,679 A | 2/1995 | Alliger |
| 5,393,526 A | 2/1995 | Castro |
| 5,405,614 A | 4/1995 | D'Angelo et al. |
| 5,415,629 A | 5/1995 | Henley |
| 5,445,609 A | 8/1995 | Lattin et al. |
| 5,451,407 A | 9/1995 | Cormier et al. |
| 5,464,387 A | 11/1995 | Haak et al. |
| 5,472,946 A | 12/1995 | Peck et al. |
| 5,501,697 A | 3/1996 | Fisher |
| 5,505,958 A | 4/1996 | Bello et al. |
| 5,512,306 A | 4/1996 | Carlsson et al. |
| 5,516,793 A | 5/1996 | Duffy |
| 5,525,351 A | 6/1996 | Dam |
| 5,545,407 A | 8/1996 | Hall et al. |
| 5,596,994 A | 1/1997 | Bro |
| 5,601,839 A | 2/1997 | Quan et al. |
| 5,616,332 A | 4/1997 | Herstein |
| 5,618,557 A | 4/1997 | Wille et al. |
| 5,653,682 A | 8/1997 | Sibalis |
| 5,656,255 A | 8/1997 | Jones |
| 5,662,920 A | 9/1997 | Santus |
| 5,686,100 A | 11/1997 | Wille et al. |
| 5,688,232 A | 11/1997 | Flower |
| 5,697,896 A | 12/1997 | McNichols et al. |
| 5,716,987 A | 2/1998 | Wille |
| 5,722,418 A | 3/1998 | Bro |
| 5,733,259 A | 3/1998 | Valcke et al. |
| 5,785,688 A | 7/1998 | Joshi et al. |
| 5,797,867 A | 8/1998 | Guerrera et al. |
| 5,820,875 A | 10/1998 | Fallon et al. |
| 5,833,466 A | 11/1998 | Borg |
| 5,843,979 A | 12/1998 | Wille et al. |
| 5,865,786 A | 2/1999 | Sibalis et al. |
| 5,876,368 A | 3/1999 | Flower |
| 5,879,292 A | 3/1999 | Sternberg et al. |
| 5,879,322 A | 3/1999 | Lattin et al. |
| 5,882,676 A | 3/1999 | Lee et al. |
| 5,908,301 A | 6/1999 | Lutz |
| 5,919,156 A | 7/1999 | Stropkay et al. |
| 5,932,240 A | 8/1999 | D'Angelo et al. |
| 5,945,123 A | 8/1999 | Hermelin |
| 5,967,789 A | 10/1999 | Segel et al. |
| 5,972,389 A | 10/1999 | Shell et al. |
| 5,993,435 A | 11/1999 | Haak et al. |
| 5,997,501 A | 12/1999 | Gross et al. |
| 6,018,679 A | 1/2000 | Dinh et al. |
| 6,019,997 A | 2/2000 | Scholz et al. |
| 6,024,981 A | 2/2000 | Khankari et al. |
| 6,034,079 A | 3/2000 | Sanberg et al. |
| 6,059,736 A | 5/2000 | Tapper |
| 6,059,753 A | 5/2000 | Faust et al. |
| 6,068,853 A | 5/2000 | Giannos et al. |
| 6,081,734 A | 6/2000 | Betz |
| 6,090,404 A | 7/2000 | Meconi et al. |
| 6,093,419 A | 7/2000 | Rolf |
| 6,120,803 A | 9/2000 | Wong et al. |
| 6,129,702 A | 10/2000 | Woias et al. |
| 6,165,155 A | 12/2000 | Jacobsen et al. |
| 6,211,194 B1 | 4/2001 | Westman et al. |
| 6,211,296 B1 | 4/2001 | Frate et al. |
| 6,238,689 B1 | 5/2001 | Rhodes et al. |
| 6,274,606 B1 | 8/2001 | Caldwell et al. |
| 6,310,102 B1 | 10/2001 | Dull et al. |
| 6,365,182 B1 | 4/2002 | Khankari et al. |
| 6,368,625 B1 | 4/2002 | Siebert et al. |
| 6,374,136 B1 | 4/2002 | Murdock |
| 6,416,471 B1 | 7/2002 | Kumar et al. |

(56) References Cited

U.S. PATENT DOCUMENTS

| | | |
|---|---|---|
| 6,417,359 B1 | 7/2002 | Crooks et al. |
| 6,423,747 B1 | 7/2002 | Lanzendörfer et al. |
| 6,436,078 B1 | 8/2002 | Svedman |
| 6,437,004 B1 | 8/2002 | Perricone |
| 6,454,708 B1 | 9/2002 | Ferguson et al. |
| 6,492,399 B1 | 12/2002 | Dull et al. |
| 6,539,250 B1 | 3/2003 | Bettinger |
| 6,567,785 B2 | 5/2003 | Clendenon |
| 6,569,449 B1 | 5/2003 | Stinchcomb et al. |
| 6,569,866 B2 | 5/2003 | Simon |
| 6,576,269 B1 | 6/2003 | Korneyev |
| 6,579,865 B2 | 6/2003 | Mak et al. |
| 6,589,229 B1 | 7/2003 | Connelly et al. |
| 6,595,956 B1 | 7/2003 | Gross et al. |
| 6,638,528 B1 | 10/2003 | Kanios |
| 6,638,543 B2 | 10/2003 | Kang et al. |
| 6,660,295 B2 | 12/2003 | Watanabe et al. |
| 6,689,380 B1 | 2/2004 | Marchitto et al. |
| 6,723,086 B2 | 4/2004 | Bassuk et al. |
| 6,723,340 B2 | 4/2004 | Gusler et al. |
| 6,746,688 B1 | 6/2004 | Kushnir et al. |
| 6,791,003 B1 | 9/2004 | Choi et al. |
| 6,799,576 B2 | 10/2004 | Farr |
| 6,849,645 B2 | 2/2005 | Majeed et al. |
| 6,861,066 B2 | 3/2005 | Van de Casteele |
| 6,867,342 B2 | 3/2005 | Johnston et al. |
| 6,887,202 B2 | 5/2005 | Currie et al. |
| 6,893,655 B2 | 5/2005 | Flanigan et al. |
| 6,900,202 B2 | 5/2005 | Imoto et al. |
| 6,911,475 B1 | 6/2005 | Villafane et al. |
| 6,998,176 B2 | 2/2006 | Morita et al. |
| 7,011,843 B2 | 3/2006 | Becher et al. |
| 7,019,622 B2 | 3/2006 | Orr et al. |
| 7,064,143 B1 | 6/2006 | Gurley et al. |
| 7,182,955 B2 | 2/2007 | Hart et al. |
| 7,196,619 B2 | 3/2007 | Perlman et al. |
| 7,229,641 B2 | 6/2007 | Cherukuri |
| 7,282,217 B1 | 10/2007 | Grimshaw et al. |
| 7,332,182 B2 | 2/2008 | Sackler |
| 7,376,700 B1 | 5/2008 | Clark et al. |
| 7,384,651 B2 | 6/2008 | Hille et al. |
| 7,384,653 B2 | 6/2008 | Wright et al. |
| 7,579,019 B2 | 8/2009 | Tapolsky et al. |
| 7,598,275 B2 | 10/2009 | Cooke et al. |
| 7,718,677 B2 | 5/2010 | Quik et al. |
| 7,780,981 B2 | 8/2010 | DiPierro et al. |
| 7,988,660 B2 | 8/2011 | Byland et al. |
| 8,003,080 B2 | 8/2011 | Rabinowitz et al. |
| 8,021,334 B2 | 9/2011 | Shekalim |
| 8,137,314 B2 | 3/2012 | Mounce et al. |
| 8,140,143 B2 | 3/2012 | Picard et al. |
| 8,192,756 B2 | 6/2012 | Berner et al. |
| 8,246,581 B2 | 8/2012 | Adams et al. |
| 8,252,321 B2 | 8/2012 | DiPierro et al. |
| 8,262,394 B2 | 9/2012 | Walker et al. |
| 8,268,475 B2 | 9/2012 | Tucholski |
| 8,285,328 B2 | 10/2012 | Caffey et al. |
| 8,303,500 B2 | 11/2012 | Raheman |
| 8,309,568 B2 | 11/2012 | Stinchcomb et al. |
| 8,372,040 B2 | 2/2013 | Huang et al. |
| 8,414,532 B2 | 4/2013 | Brandt et al. |
| 8,440,220 B2 | 5/2013 | Gale et al. |
| 8,440,221 B2 | 5/2013 | Zumbrunn et al. |
| 8,441,411 B2 | 5/2013 | Tucholski et al. |
| 8,445,010 B2 | 5/2013 | Anderson et al. |
| 8,449,471 B2 | 5/2013 | Tran |
| 8,517,988 B2 | 8/2013 | Smith |
| 8,545,445 B2 | 10/2013 | Kamen et al. |
| 8,574,188 B2 | 11/2013 | Potter et al. |
| 8,586,079 B2 | 11/2013 | Hansted et al. |
| 8,589,174 B2 | 11/2013 | Nelson et al. |
| 8,614,278 B2 | 12/2013 | Loubert et al. |
| 8,632,497 B2 | 1/2014 | Yodfat et al. |
| 8,666,781 B2 | 3/2014 | Hanina et al. |
| 8,673,346 B2 | 3/2014 | Zumbrunn et al. |
| 8,684,922 B2 | 4/2014 | Tran |
| 8,688,189 B2 | 4/2014 | Shennib |
| 8,690,827 B2 | 4/2014 | Edwards et al. |
| 8,696,637 B2 | 4/2014 | Ross |
| 8,703,175 B2 | 4/2014 | Kanios et al. |
| 8,703,177 B2 | 4/2014 | Finn et al. |
| 8,722,233 B2 | 5/2014 | Tucholski |
| 8,727,745 B2 | 5/2014 | Rush et al. |
| 8,741,336 B2 | 6/2014 | DiPierro et al. |
| 8,747,348 B2 | 6/2014 | Yodfat et al. |
| 8,753,315 B2 | 6/2014 | Alferness et al. |
| 8,773,257 B2 | 7/2014 | Yodfat et al. |
| 8,814,822 B2 | 8/2014 | Yodfat et al. |
| 8,862,223 B2 | 10/2014 | Yanaki |
| 8,864,727 B2 | 10/2014 | Lee |
| 8,865,207 B2 | 10/2014 | Kanios et al. |
| 8,872,663 B2 | 10/2014 | Forster |
| 8,876,802 B2 | 11/2014 | Grigorov |
| 8,956,644 B2 | 2/2015 | Yum et al. |
| 8,962,014 B2 | 2/2015 | Prinz et al. |
| 8,986,253 B2 | 3/2015 | DiPerna |
| 8,999,356 B1 | 4/2015 | Ramirez et al. |
| 9,023,392 B2 | 5/2015 | Koo et al. |
| 9,044,582 B2 | 6/2015 | Chang et al. |
| 9,050,348 B2 | 6/2015 | Kydonieus et al. |
| 9,078,833 B2 | 7/2015 | Audett |
| 9,111,085 B1 | 8/2015 | Darmour et al. |
| 9,114,240 B2 | 8/2015 | Horstmann et al. |
| 9,155,712 B2 | 10/2015 | Kanios et al. |
| 9,233,203 B2 | 1/2016 | Moberg et al. |
| 9,238,001 B2 | 1/2016 | Weyer et al. |
| 9,238,108 B2 | 1/2016 | Edwards et al. |
| 9,248,104 B2 | 2/2016 | Valia et al. |
| 9,289,397 B2 | 3/2016 | Wright |
| 9,308,202 B2 | 4/2016 | Hille et al. |
| 9,314,527 B2 | 4/2016 | Cottrell et al. |
| 9,373,269 B2 | 6/2016 | Bergman et al. |
| 9,380,698 B1 | 6/2016 | Li et al. |
| 9,418,497 B2 * | 8/2016 | Ingle ............... G07C 9/00896 |
| RE46,217 E | 11/2016 | Huang et al. |
| 9,513,666 B2 | 12/2016 | Li et al. |
| 9,549,903 B2 | 1/2017 | Hille et al. |
| 9,555,226 B2 | 1/2017 | Zumbrunn et al. |
| 9,555,227 B2 | 1/2017 | Dipierro |
| 9,623,017 B2 | 4/2017 | Barbier et al. |
| 9,636,457 B2 | 5/2017 | Newberry et al. |
| 9,655,843 B2 | 5/2017 | Finn et al. |
| 9,656,441 B2 | 5/2017 | LeDonne et al. |
| 9,669,199 B2 | 6/2017 | DiPierro et al. |
| 9,693,689 B2 | 7/2017 | Gannon et al. |
| 9,700,552 B2 | 7/2017 | Weimann |
| 9,717,698 B2 | 8/2017 | Horstmann et al. |
| 9,782,082 B2 | 10/2017 | Gannon et al. |
| 9,795,681 B2 | 10/2017 | Abreu |
| 9,867,539 B2 | 1/2018 | Heikenfeld et al. |
| 9,895,320 B2 | 2/2018 | Ogino et al. |
| 9,949,935 B2 | 4/2018 | Murata |
| 9,974,492 B1 | 5/2018 | Dicks et al. |
| 9,993,203 B2 | 6/2018 | Mei et al. |
| 10,004,447 B2 | 6/2018 | Shen et al. |
| 10,034,841 B2 | 7/2018 | Müller et al. |
| 2001/0022978 A1 | 9/2001 | Lacharriere et al. |
| 2001/0026788 A1 | 10/2001 | Piskorz |
| 2002/0002189 A1 | 1/2002 | Smith et al. |
| 2002/0106329 A1 | 8/2002 | Leslie |
| 2002/0127256 A1 | 9/2002 | Murad |
| 2002/0165170 A1 | 11/2002 | Wilson et al. |
| 2002/0169439 A1 | 11/2002 | Flaherty |
| 2002/0182238 A1 | 12/2002 | Creton |
| 2003/0004187 A1 | 1/2003 | Bedard et al. |
| 2003/0065294 A1 | 4/2003 | Pickup et al. |
| 2003/0065924 A1 | 4/2003 | Wuidart et al. |
| 2003/0083645 A1 | 5/2003 | Angel et al. |
| 2003/0087937 A1 | 5/2003 | Lindberg |
| 2003/0119879 A1 | 6/2003 | Landh et al. |
| 2003/0159702 A1 | 8/2003 | Lindell et al. |
| 2004/0019321 A1 | 1/2004 | Sage et al. |
| 2004/0034068 A1 | 2/2004 | Warchol et al. |
| 2004/0037879 A1 | 2/2004 | Adusumilli et al. |

(56) References Cited

U.S. PATENT DOCUMENTS

| | | |
|---|---|---|
| 2004/0052843 A1 | 3/2004 | Lerner et al. |
| 2004/0062802 A1 | 4/2004 | Hermelin |
| 2004/0138074 A1 | 7/2004 | Ahmad et al. |
| 2004/0166159 A1 | 8/2004 | Han et al. |
| 2004/0191322 A1 | 9/2004 | Hansson |
| 2004/0194793 A1 | 10/2004 | Lindell et al. |
| 2004/0229908 A1 | 11/2004 | Nelson |
| 2004/0241218 A1 | 12/2004 | Tavares et al. |
| 2004/0253249 A1 | 12/2004 | Rudnic et al. |
| 2004/0259816 A1 | 12/2004 | Pandol et al. |
| 2005/0002806 A1 | 1/2005 | Fuechslin et al. |
| 2005/0014779 A1 | 1/2005 | Papke |
| 2005/0021092 A1 | 1/2005 | Yun et al. |
| 2005/0034842 A1 | 2/2005 | Huber et al. |
| 2005/0048020 A1 | 3/2005 | Wille |
| 2005/0053665 A1 | 3/2005 | Ek et al. |
| 2005/0113452 A1 | 5/2005 | Flashner Barak et al. |
| 2005/0141346 A1 | 6/2005 | Rawls et al. |
| 2005/0151110 A1 | 7/2005 | Minor et al. |
| 2005/0159419 A1 | 7/2005 | Stephenson et al. |
| 2006/0024358 A1 | 2/2006 | Santini et al. |
| 2006/0036209 A1 | 2/2006 | Subramony et al. |
| 2006/0122577 A1 | 6/2006 | Poulsen et al. |
| 2006/0167039 A1 | 7/2006 | Nguyen et al. |
| 2006/0184093 A1 | 8/2006 | Phipps et al. |
| 2006/0188859 A1 | 8/2006 | Yakobi |
| 2006/0206054 A1 | 9/2006 | Shekalim |
| 2007/0026054 A1 | 2/2007 | Theobald et al. |
| 2007/0042026 A1 | 2/2007 | Wille |
| 2007/0065365 A1 | 3/2007 | Kugelmann et al. |
| 2007/0086275 A1 | 4/2007 | Robinson et al. |
| 2007/0088338 A1 | 4/2007 | Ehwald et al. |
| 2007/0149952 A1 | 6/2007 | Bland et al. |
| 2007/0154336 A1 | 7/2007 | Miyazaki et al. |
| 2007/0168501 A1 | 7/2007 | Cobb et al. |
| 2007/0179172 A1 | 8/2007 | Becker et al. |
| 2007/0191815 A1 | 8/2007 | DiPierro |
| 2007/0250018 A1 | 10/2007 | Adachi et al. |
| 2007/0256684 A1 | 11/2007 | Kelliher et al. |
| 2007/0260491 A1 | 11/2007 | Palmer et al. |
| 2007/0279217 A1 | 12/2007 | Venkatraman et al. |
| 2007/0299401 A1 | 12/2007 | Alferness et al. |
| 2008/0008747 A1 | 1/2008 | Royds |
| 2008/0138294 A1 | 6/2008 | Gonda |
| 2008/0138398 A1 | 6/2008 | Gonda |
| 2008/0138399 A1 | 6/2008 | Gonda |
| 2008/0138423 A1 | 6/2008 | Gonda |
| 2008/0152592 A1 | 6/2008 | Rebec |
| 2008/0195946 A1 | 8/2008 | Peri-Glass |
| 2008/0201174 A1 | 8/2008 | Ramasubramanian et al. |
| 2008/0233178 A1 | 9/2008 | Reidenberg et al. |
| 2008/0274168 A1 | 11/2008 | Baker et al. |
| 2008/0319272 A1 | 12/2008 | Patangay et al. |
| 2009/0005009 A1 | 1/2009 | Marsili |
| 2009/0024004 A1 | 1/2009 | Yang |
| 2009/0062754 A1 | 3/2009 | Tang |
| 2009/0118710 A1 | 5/2009 | Kortzeborn |
| 2009/0169631 A1 | 7/2009 | Zamloot et al. |
| 2009/0246265 A1 | 10/2009 | Stinchcomb et al. |
| 2009/0247985 A1 | 10/2009 | Melsheimer et al. |
| 2009/0259176 A1 | 10/2009 | Yairi |
| 2010/0003653 A1 | 1/2010 | Brown |
| 2010/0068250 A1 | 3/2010 | Anderson et al. |
| 2010/0114008 A1 | 5/2010 | Marchitto et al. |
| 2010/0145303 A1 | 6/2010 | Yodfat et al. |
| 2010/0179473 A1 | 7/2010 | Genosar |
| 2010/0196463 A1 | 8/2010 | Quik et al. |
| 2010/0248198 A1 | 9/2010 | Seidman et al. |
| 2010/0273738 A1 | 10/2010 | Valcke et al. |
| 2010/0280432 A1 | 11/2010 | DiPierro et al. |
| 2011/0004072 A1* | 1/2011 | Fletcher .............. A61B 5/0002 600/300 |
| 2011/0053129 A1 | 3/2011 | Basson et al. |
| 2011/0054285 A1 | 3/2011 | Searle et al. |
| 2011/0109439 A1 | 5/2011 | Borlenghi |
| 2011/0137255 A1 | 6/2011 | Nielsen et al. |
| 2011/0152635 A1 | 6/2011 | Morris et al. |
| 2011/0153360 A1 | 6/2011 | Hanina et al. |
| 2011/0160640 A1 | 6/2011 | Yanaki |
| 2011/0241446 A1 | 10/2011 | Tucholski |
| 2011/0245633 A1 | 10/2011 | Goldberg et al. |
| 2011/0245783 A1 | 10/2011 | Stinchcomb et al. |
| 2011/0250576 A1 | 10/2011 | Hester |
| 2011/0256517 A1 | 10/2011 | Swanson |
| 2011/0264028 A1 | 10/2011 | Ramdas et al. |
| 2011/0268809 A1 | 11/2011 | Brinkley et al. |
| 2011/0275987 A1 | 11/2011 | Caffey et al. |
| 2012/0046644 A1 | 2/2012 | Ziaie et al. |
| 2012/0123387 A1 | 5/2012 | Gonzalez et al. |
| 2012/0156138 A1 | 6/2012 | Smith |
| 2012/0171277 A1 | 7/2012 | Royds |
| 2012/0178065 A1 | 7/2012 | Naghavi et al. |
| 2012/0203573 A1 | 8/2012 | Mayer et al. |
| 2012/0209223 A1 | 8/2012 | Salman et al. |
| 2012/0221251 A1 | 8/2012 | Rosenberg et al. |
| 2012/0244503 A1 | 9/2012 | Neveldine |
| 2012/0302844 A1 | 11/2012 | Schnidrig et al. |
| 2012/0316896 A1* | 12/2012 | Rahman .............. G06Q 50/24 705/3 |
| 2012/0329017 A1 | 12/2012 | Pham |
| 2013/0017259 A1 | 1/2013 | Azhir |
| 2013/0123719 A1 | 5/2013 | Mao et al. |
| 2013/0158430 A1 | 6/2013 | Aceti et al. |
| 2013/0178826 A1 | 7/2013 | Li |
| 2013/0190683 A1 | 7/2013 | Hanson et al. |
| 2013/0216989 A1 | 8/2013 | Cuthbert |
| 2013/0253430 A1 | 9/2013 | Kouyoumjian et al. |
| 2013/0302398 A1 | 11/2013 | Ambati et al. |
| 2013/0311917 A1 | 11/2013 | Bar-or et al. |
| 2013/0317384 A1 | 11/2013 | Le |
| 2013/0328572 A1 | 12/2013 | Wang et al. |
| 2013/0345633 A1 | 12/2013 | Chong |
| 2014/0046288 A1 | 2/2014 | Geipel et al. |
| 2014/0073883 A1 | 3/2014 | Rao et al. |
| 2014/0088554 A1 | 3/2014 | Li et al. |
| 2014/0099614 A1 | 4/2014 | Hu et al. |
| 2014/0100241 A1 | 4/2014 | Slater et al. |
| 2014/0200525 A1 | 7/2014 | DiPierro |
| 2014/0206327 A1 | 7/2014 | Ziemianska et al. |
| 2014/0207047 A1 | 7/2014 | DiPierro et al. |
| 2014/0207048 A1 | 7/2014 | DiPierro et al. |
| 2014/0228736 A1 | 8/2014 | Eppstein et al. |
| 2014/0237028 A1 | 8/2014 | Messenger et al. |
| 2014/0240124 A1 | 8/2014 | Bychkov |
| 2014/0272844 A1 | 9/2014 | Hendriks et al. |
| 2014/0272845 A1 | 9/2014 | Hendriks et al. |
| 2014/0272846 A1 | 9/2014 | Richling |
| 2014/0275135 A1 | 9/2014 | Genov et al. |
| 2014/0275932 A1 | 9/2014 | Zadig |
| 2014/0276127 A1 | 9/2014 | Ferdosi et al. |
| 2014/0279740 A1 | 9/2014 | Wernevi et al. |
| 2014/0303574 A1 | 10/2014 | Knutson |
| 2014/0365408 A1 | 12/2014 | Snyder et al. |
| 2014/0378943 A1 | 12/2014 | Geipel |
| 2015/0209783 A1 | 7/2015 | Ingber et al. |
| 2015/0273148 A1 | 10/2015 | Sexton et al. |
| 2015/0310760 A1 | 10/2015 | Knotts et al. |
| 2016/0030412 A1 | 2/2016 | Azhir |
| 2016/0220798 A1 | 8/2016 | Netzel et al. |
| 2016/0227361 A1 | 8/2016 | Booth et al. |
| 2016/0228383 A1 | 8/2016 | Zhang et al. |
| 2016/0235916 A1 | 8/2016 | Edwards et al. |
| 2016/0310664 A1 | 10/2016 | McKenzie et al. |
| 2016/0317057 A1 | 11/2016 | Li et al. |
| 2016/0339174 A1 | 11/2016 | Shapley et al. |
| 2016/0346462 A1 | 12/2016 | Adams et al. |
| 2017/0007550 A1 | 1/2017 | Enscore et al. |
| 2017/0079932 A1 | 3/2017 | Emgenbroich et al. |
| 2017/0100572 A1 | 4/2017 | Zumbrunn et al. |
| 2017/0100573 A1 | 4/2017 | DiPierro |
| 2017/0182299 A1 | 6/2017 | DiPierro et al. |
| 2017/0189348 A1 | 7/2017 | Lee et al. |
| 2017/0189534 A1 | 7/2017 | Lee et al. |
| 2017/0207825 A1 | 7/2017 | Belogolovy |

(56) References Cited

U.S. PATENT DOCUMENTS

| | | | |
|---|---|---|---|
| 2017/0209429 A1 | 7/2017 | Stinchcomb et al. |
| 2017/0224911 A1 | 8/2017 | DiPierro et al. |
| 2017/0249433 A1 | 8/2017 | Hagen et al. |
| 2017/0296317 A1 | 10/2017 | Gordon |
| 2017/0351840 A1 | 12/2017 | Goguen |
| 2018/0110975 A1 | 4/2018 | Ivanoff et al. |
| 2018/0165566 A1 | 6/2018 | Rogers et al. |
| 2018/0197637 A1 | 7/2018 | Chowdhury |
| 2019/0054235 A1 | 2/2019 | DiPierro et al. |

FOREIGN PATENT DOCUMENTS

| | | |
|---|---|---|
| CA | 2142871 A1 | 3/1994 |
| CN | 1704056 A | 12/2005 |
| DE | 19958554 A1 | 1/2001 |
| DE | 10105759 C1 | 10/2001 |
| DE | 10103158 A1 | 8/2002 |
| EP | 0314528 B1 | 12/1992 |
| EP | 0354554 B1 | 1/1994 |
| EP | 0726005 A1 | 8/1996 |
| EP | 0612525 B1 | 9/2001 |
| EP | 1815784 A1 | 8/2007 |
| EP | 1977746 B1 | 7/2014 |
| EP | 1662989 B1 | 9/2014 |
| EP | 3016586 A2 | 5/2016 |
| GB | 1528391 A | 10/1978 |
| GB | 2030862 A | 4/1980 |
| GB | 2142822 A | 1/1985 |
| GB | 2230439 A | 10/1990 |
| JP | 02202813 A | 8/1990 |
| JP | 09512006 A | 12/1997 |
| JP | 2002092180 A | 3/2002 |
| JP | 2005525147 A | 8/2005 |
| JP | 2009544338 A | 12/2009 |
| JP | 2010518914 A | 6/2010 |
| JP | 2016202904 A | 12/2016 |
| WO | WO86/07269 A1 | 12/1986 |
| WO | WO88/003803 A1 | 6/1988 |
| WO | WO91/14441 A1 | 10/1991 |
| WO | WO94/010987 A1 | 5/1994 |
| WO | WO95/06497 A1 | 3/1995 |
| WO | WO97/11741 A1 | 4/1997 |
| WO | WO97/18782 A1 | 5/1997 |
| WO | WO97/028801 A1 | 8/1997 |
| WO | WO97/034605 A1 | 9/1997 |
| WO | WO97/042941 A2 | 11/1997 |
| WO | WO98/46093 A1 | 10/1998 |
| WO | WO99/066916 A1 | 12/1999 |
| WO | WO00/035279 A1 | 6/2000 |
| WO | WO00/035456 A1 | 6/2000 |
| WO | WO00/74763 A2 | 12/2000 |
| WO | WO00/74933 A1 | 12/2000 |
| WO | WO01/005459 A1 | 1/2001 |
| WO | WO01/037814 A1 | 5/2001 |
| WO | WO02/076211 A1 | 10/2002 |
| WO | WO03/022349 A2 | 3/2003 |
| WO | WO03/026655 A1 | 4/2003 |
| WO | WO03/055486 A1 | 7/2003 |
| WO | WO03/061656 A1 | 7/2003 |
| WO | WO03/070191 A1 | 8/2003 |
| WO | WO03/097146 A1 | 11/2003 |
| WO | WO2004/024124 A1 | 3/2004 |
| WO | WO2004/073429 A1 | 9/2004 |
| WO | WO2005/023227 A2 | 3/2005 |
| WO | WO2005/079161 A2 | 9/2005 |
| WO | WO2006/069097 A2 | 6/2006 |
| WO | WO2007/013975 A2 | 2/2007 |
| WO | WO2007/041544 A1 | 4/2007 |
| WO | WO2007/104574 A2 | 9/2007 |
| WO | WO2007/104575 A2 | 9/2007 |
| WO | WO2007/133141 A1 | 11/2007 |
| WO | WO2008/024408 A2 | 2/2008 |
| WO | WO2008/054788 A2 | 5/2008 |
| WO | WO2008/069921 A2 | 6/2008 |
| WO | WO2008/069970 A2 | 6/2008 |
| WO | WO2008/069972 A2 | 6/2008 |
| WO | WO2008/135283 A1 | 11/2008 |
| WO | WO2009/136304 A2 | 11/2009 |
| WO | WO2011/088072 A2 | 7/2011 |
| WO | WO2012/012846 A1 | 2/2012 |
| WO | WO2012/101060 A1 | 8/2012 |
| WO | WO2013/093666 A1 | 6/2013 |
| WO | WO2013/168068 A1 | 11/2013 |
| WO | WO2014/001877 A1 | 1/2014 |
| WO | WO2014/043502 A1 | 3/2014 |
| WO | WO2016/081616 A2 | 5/2016 |
| WO | WO2016/161416 A1 | 10/2016 |
| WO | WO2017/053938 A1 | 3/2017 |
| WO | WO2017/125455 A1 | 7/2017 |
| WO | WO2018/026759 A1 | 2/2018 |

OTHER PUBLICATIONS

Bricker et al.; Randomized controlled pilot trial of a smartphone app for smoking cessation using acceptance and commitment therapy; Drug and Alcohol Dependence; 143; pp. 87-94; Oct. 1, 2014 (Author Manuscript).

Bruguerolle; Chronopharmacokinetics; Clin Pharmacokinet; 35(2); pp. 83-94; Aug. 1998.

Dockser-Marcus, A.; New research shows drugs work best at certain times; The Wall Street Journal; 6 pgs.; May 27, 2003; (http://www.wsj.com/articles/SB105397312486508700).

Domino et al.; Nicotine alone and in combination with L-DOPA methyl ester or the D(2) agonist N-0923 in MPTP-induced chronic hemiparkinsonian monkeys; Exp Neurol; 158(2); pp. 414-421; Aug. 1999.

Dutil; Benzoyl Peroxide: Enhancing antibiotic efficacy in acne management; Skin Therapy Letter; 15(1); pp. 5-7; Nov./Dec. 2010.

Ethicon Endo-Surgery, Inc.; Sedasys® Computer-assisted personalized sedation system essential product information; retrieved May 12, 2015 from the internet (http://www.sedasys.com/explore-the-system/essential-product-information); 2 pgs.

Gennaro (Editor); Remington: The Science and Practice of Pharmacy; 19th Ed.; Mack Publishing Co.; Easton, PA; p. 1582-1584; Jun. 1995.

Giannos; Chapter 20: Pulsatile fSmartf Drug Delivery, in Skin Delivery Systems: Transdermals, Dermatologicals, and Cosmetic Actives; (ed.) Wille, Jr; Blackwell Pub.; Oxford, UK; pp. 327-357; Jun. 2006.

Gries et al.; Importance of Chronopharmacokinetics in Design and Evaluation of Transdermal Drug Delivery Systems; J Pharmoacol Exp Ther; 285(2); pp. 457-463; May 1998.

Guy; Current status and future prospects of transdermal drug delivery; Pharm Res; 13(12); pp. 1765-1769; Dec. 1996.

Halberg et al.; Chronomics: circadian and circaseptan timing of radiotherapy, drugs, calories, perhaps nutriceuticals and beyond; Journal of Experimental Therapeutics and Oncology; 3(5); pp. 223-260; Sep. 2003.

Heffner et al.; Feature-level analysis of a novel smartphone applicationn for smoking cessation; Am. J. Drug Alcohol Abuse; 41(1); pp. 68-73; Jan. 2015 (Author Manuscript).

Hrushesky; Temporally optimizable delivery systems: sine qua non for the next therapeutic revolution; J Cont Rel; 19(1-3); pp. 363-368; Mar. 1992.

Huang et al.; Inhibitory effects of curcumin on in vitro lipoxygenase and cyclooxygenase activities in mouse epidermis; Cancer Res; 51(3); pp. 813-819; Feb. 1991.

Kalish et al.; Prevention of contact hypersensitivity to topically applied drugs by ethacrynic acid: potential application to transdermal drug delivery; J. Controll Rel; 48(1); pp. 79-87; Sep. 1997.

Kalish et al.; Sensitization of mice to topically applied drugs: albuterol, chlorpheniramine, clonidine and nadolol; Contact Dermatitis; 35(2); pp. 76-82; Aug. 1996.

Kennelly; Microcontrollers drive home drug delivery; 3 pgs; posted Jul. 2014; (retrieved Jul. 26, 2016 from the internet: http://electronicsmaker.com/microcontrollers-drive-home-drug-delivery-2.

(56) References Cited

OTHER PUBLICATIONS

Kotwal; Enhancement of intophoretic transport of diphenhydramine hydrochloride thermosensitive gel by optimization of pH, polymer concentration, electrode design, and pulse rate; AAPS PharmSciTech; 8(4); pp. 320-325; Oct. 2007.
Kydonieus et al. (Editors); Biochemical Modulation of Skin Reactions; CRC Press; Boca Ratan, FL; pp. 9-10; Dec. 1999.
Labrecque, G. et al.; Chronopharmacokinetics; Pharmaceutical News; 4(2); pp. 17-21; 1997.
Lamberg; Chronotherapeutics: Implications for drug therapy; American Pharmacy; NS31(11); pp. 20-23; Nov. 1991.
Laser et al.; A review of micropumps; J. of Micromech. And Microeng.; 14; pp. R35-R64; Apr. 2004.
Lemay et al.; Lack of efficacy of a nicotine transdermal treatment on motor and cognitive deficits in Parkinson's disease; Prog Neuropsychopharmacol Biol Psychiatry; 28(1); pp. 31-39; Jan. 2004.
Lemmer; Clinical Chronopharmacology: The Importance of Time in Drug Treatment, in Ciba Foundation Symposium 183—Circadian Clocks and their Adjustment (eds. Chadwick and Ackrill); John Wiley & Sons, Inc.; pp. 235-253; Apr. 1995.
Lemmer; Implications of chronopharmacokinetics for drug delivery: antiasthmatics, H2-blockers and cardiovascular active drugs; Adv Drug Del Rev; 6(1); pp. 83-100; Jan./Feb. 1991.
Lemmer; The clinical relevance of chronopharmacology in therapeutics; Pharmacological Research; 33(2); pp. 107-115; Feb. 1996.
LeWitt et al.; New developments in levodopa therapy; Neurology; 62(No. 1, Suppl. 1); pp. S9-S16; Jan. 2004.
Maillefer et al.; A high-performance silicon micropump for an implantable drug delivery system; 12th IEEE Int'l Conf. on Micro Electro Mechanical Systems; MEMS '99; Orlando, FL; pp. 541-546; Jan. 1999.
Medtronic; MiniMed Paradigm® Veo(TM) System (product info.); retrieved May 12, 2015from the internet: (http://www.medtronic.co.uk/your-health/diabetes/device/insulin-pumps/paradigm-veo-pump/); 3 pgs.
Molander et al.; Reduction of tobacco withdrawal symptoms with a sublingual nicotine tablet: A placebo controlled study; Nictonie & Tob. Res.; 2(2); pp. 187-191; May 2000.
Murphy et al.; Transdermal drug delivery systems and skin sensitivity reactions. Incidence and management; Am. J. Clin Dermatol.; 1(6); pp. 361-368; Nov./Dec. 2000.
Mutalik et al.; Glibenclamide transdermal patches: physicochemical, pharmacodynamic, and pharmacokinetic evaluation; J Pharm Sci; 93(6); pp. 1577-1594; Jun. 2004.
Mutalik et al.; Glipizide matrix transdermal systems for diabetes mellitus: preparation, in vitro and preclinical studies; Life Sci; 79(16; pp. 1568-1567; Sep. 2006.
Nakadate et al.; Effects of chalcone derivatives on lipoxygenase and cyclooxygenase activities of mouse epidermis; Prostaglandins; 30(3); pp. 357-368; Sep. 1985.
Newmark; Plant phenolics as potential cancer prevention agents; Chapter 3 in Dietary Phytochemicals in Cancer Prevention; Chap. 3; Adv. Exp. Med. Biol. 401; pp. 25-34; © 1996.
Ohdo; Changes in toxicity and effectiveness with timing of drug administration: implications for drug safety; Drug Safety; 26(14); pp. 999-1010; Dec. 2003.
Olsson et al.; A valve-less planar pump in silicon; IEEE; The 8th International Conference on Solid-State Sensors and Actuators; vol. 2; pp. 291-294, Jun. 1995.
Olsson et al.; An improved valve-less pump fabricated using deep reactive ion etching; Proc. Of the IEEE, 9th Int'l Workshop on MEMS; San Diego, CA; pp. 479-484; Feb. 11-15, 1996.
Priano et al.; Nocturnal anomalous movement reduction and sleep microstructure analysis in parkinsonian patients during 1-night transdermal apomorphine treatment; Neurol Sci.; 24(3); pp. 207-208; Oct. 2003.
Prosise et al.; Effect of abstinence from smoking on sleep and daytime sleepiness; Chest; 105(4); pp. 1136-1141; Apr. 1994.
Quik et al.; L-DOPA treatment modulates nicotinic receptors in monkey striatum; Mol Pharmacol; 64(3); pp. 619-628; Sep. 2003.
Quik et al.; Nicotine and nicotinic receptors; relevance to Parkinson's disease; Neurotoxicology; 23(4-5); pp. 581-594; Oct. 2002.
Quik; Smoking, nicotine and Parkinson's disease; Trends in Neurosciences; 27(9); pp. 561-568; Sep. 2004.
Redfern et al.; Circadian rhythms, jet lag, and chronobiotics: An overview; Chronobiology International; 11(4); pp. 253-265; Aug. 1994.
Reinberg; Concepts of Circadian Chronopharmacology; Annals of the New York Academy of Sciences; 618 (Temporal Control of Drug Delivery); pp. 102-115; Feb. 1991.
Shin et al.; Enhanced bioavailability of triprolidine from the transdermal TPX matrix system in rabbits; Int. J. Pharm.; 234(1-2); pp. 67-73; Mar. 2002.
Singer et al.; Nightmares in patients with Alzheimer's disease caused by donepezil: Therapeutic effect depends on the time of intake; Nervenarzt; 76(9); pp. 1127-1129; Sep. 2005 (Article in German w/ Eng. Summary).
Star Micronics Co., Ltd; Prototype Diaphragm Micro Pump SDMP305 (specifications); retrieved May 12, 2015 from the internet archive as of Jul. 2006 (http://www.star-m.jp/eng/products/develop/de07.htm); 3 pgs.
Thiele et al. (Ed.); Oxidants and Antioxidants in Cutaneous Biology: Current Problems in Dermatology (Book 29); S. Karger; 196 pgs.; Feb. 2001.
Wille et al.; cis-urocanic Acid Induces Mast Cell Degranulation and Release of Preformed TNF-alpha: A Possible Mechanism Linking UVB and cis-urocanic Acid to Immunosuppression of Contact Hypersensitivity; Skin Pharm Appl Skin Physiol; 12(1-2); pp. 18-27; Jan. 1999.
Wille et al.; Inhibition of irritation and contact hypersensitivity by ethacrynic acid; Skin Pharm Appl Skin Physiol; 11(4-5); pp. 279-288; Jul. 1998.
Wille et al.; Inhibition of Irritation and Contact Hypersensitivity by Phenoxyacetic Acid Methyl Ester in Mice; Skin Pharm Appl Skin Physiol; 13(2); pp. 65-74; Mar. 2000.
Wille et al.; Several different ion channel modulators abrogate contact hypersensitivity in mice; Skin Pharm Appl Skin Physiol; 12(1-2); pp. 12-17; Jan. 1999.
Wille, J.; Novel topical delivery system for plant derived hydrophobic anti-irritant active (presentation abstract No. 273); 226th ACS National Meeting; New York, NY; Sep. 7-11, 2003.
Wille; In Closing: an editorial on Plant-Derived Anti-irritants. Cosmetics & Toiletries, 118 (8), Aug. 2003.
Wille; Novel plant-derived anti-irritants; (presented Dec. 5-6, 2002 at the 2002 Ann. Scientific Mtg. & Tech. Showcase); J. Cosmet. Sci.; 54; pp. 106-107; Jan./Feb. 2003.
Wille; Thixogel: Novel topical delivery system for hydrophobic plant actives; in Rosen (Ed.) Delivery System Handbook for Personal Care and Cosmetic Products; 1st Ed.; ISBN: 978-0-8155-1504-3; pp. 762-794; Sep. 2005.
Youan; Chronopharmaceutics: gimmick or clinically relevant approach to drug delivery?; J Cont Rel; 98(3); pp. 337-353; Aug. 2004.
Yun et al.; A distributed memory MIMD multi-computer with reconfigurable custom computing capabilities; IEEE; Proc. Int'l Conf. on Parallel and Distributed Systems; pp. 8-13; Dec. 10-13, 1997.
Abood et al.; Structure-activity studies of carbamate and other esters: agonists and antagonists to nicotine; Pharmacology Biochemistry and Behavior; 30(2); pp. 403-408; Jun. 1988.
Baldessarini et al.; Preclinical studies of the pharmacology of aporphines; In: Gessa GL, Corsini GU, eds.; Apomorphine and other dopaminomi-'metics vol. 1, Basic pharmacology; New York: Raven Press; pp. 219-228; (year of pub. sufficiently earlier than effective US filing date and any foreign priority date) 1981.
Jarvik et al.; Inhibition of cigarette smoking by orally administered nicotine; Clinical Pharmacology and Therapeutics; 11(4); pp. 574-576; Jul. 1, 1970.
Kiwi Drug; Buy nicorette microtabs; 3 pages; retrieved from the internet (www.kiwidrug.com/search/nicorette_microtabs); on Jul. 26, 2018.

(56) References Cited

OTHER PUBLICATIONS

Lieberman; Compression—coated and layer tablets; Pharmaceutical Dosage forms; vol. 1, 2nd ed.; Marcel Dekker Inc.; pp. 266-271; (year of pub. sufficiently earlier than effective US filing date and any foreign priority date) 1989.
McNeil Sweden AB. Package Leaflet: Information for the user. Nicorette Microtab Lemon 2mg sublingual tablets. (This leaflet was last approved in Apr. 16, 2008). retrived from ( www.lakemedelsverket. se/SPC_PIL/Pdf/enhumpil/Nicorette%20Microtab%20Lemon% 202mg%20sublingual%20tablet%20ENG.pdf.) Accessed Aug. 19, 2010.
Meissner et al.; Priorities in parkinson's disease research; Nature reviews Drug Discovery; 10(5); pp. 377-393; May 1, 2011.
Merck manual of therapy and diagnosis; 17th edition. Merck Research Laboratories; pp. 1466-1471; (year of pub. sufficiently earlier than effective US filing date and any foreign priority date) 1999.
Silver et al.; Transdermal nicotine and haloperidol in Tourette's disorder: a double-blind placebo-controlled study; Journal of Clinical Psychiatry; 62(9); pp. 707-714; Sep. 1, 2001.
Strong et al.; Genotype and smoking history affect risk of levodopa-induced dyskinesias in parkinson's disease; Movement Disorders; 21(5); pp. 654-659; May 1, 2006.
Tolosa et al.; Antagonism by piperidine of levodopa effects in Parkinson disease; Neurology; 27(9); pp. 875-877; Sep. 1, 1977.
Villafane et al.; Long-term nicotine administration can improve Parkinson's disease: report of a case after three years of treatment; Revista Neurologica Argentina; 27(2); pp. 95-97; (year of pub. sufficiently earlier than effective US filing date and any foreign priority date) 2002.
Warburton et al.; Facilitation of learning and state dependency with nicotine; Psychoparmacology; 89(1); pp. 55-59; May 1, 1986.
Wesnes et al.; Effects of scopolamine and nicotine on human rapid information processing performance; Psychoparmacology; 82(3); pp. 147-150; Sep. 1, 1984.
Bordia et al.; Continuous and intermittent nicotine treatment reduces L-3 4-dihydroxyphenyalanine (L-DOPA)-induced dyskinesias in rat model of Parkinson's diseases; Journal of Pharmacology ans Experimental Therapeutics; 327(1); pp. 239-247; Oct. 1, 2008.
Calabres et al.; Levodopa-induced dyskinesias inpatients with parkinson's disease: filling the bench-to-bedside gap; The Lancet Neurology; 9(11); pp. 1106-1117; Nov. 1, 2010.
Angulo et al.; Oral nicotine in treatment of primary sclerosing cholangitis: a pilot study; Digestive diseases and sciences; 44(3); pp. 602-607; Mar. 1, 1999.
Benowitz et al.; Sources of variability in nicotine and cotinine levels with use of nicotine nasal spray, transdermal nicotine, and cigarette smoking; British Journal of Clinical Pharmacology; 43(3); pp. 259-267; Mar. 1, 1997.
Bordia et al.; Partial recovery of striatal nicotinic receptors in l-methyl-4-phenyl-1,2,3,6-tetrahydropyridine (MPTP)-lesioned monkeys with chronic oral nicotinic; The Journal of Pharmacology and Experimental Therapeutics; 319(1); pp. 285-292; Oct. 1, 2006.
Bove et al.; Toxin-induced models of Parkinson's disease; NeuroRx; 2(3); pp. 484-494; Jul. 31, 2005.
Brotchie et al.; Levodopa-induced dyskinesia in Parkinson's disease; Journal of Neural Transmission; 112(3); pp. 359-391; Mar. 1, 2005.
Damaj et al.; Antinociceptive responses to nicotinic acetylcholine receptor ligands after systemic and intrathecal administration in mice; Journal of Pharmacology and Experimental Therapeutics; 284(3); pp. 1058-1065; Mar. 1, 1998.
Davie; A review of Parkinson's disease. British Medical Bulletin 2008 86(1): 109-127; Apr. 8, 2008.
De La Fuente et al.; The placebo effect in Parkinson's disease; Trends in Neuroscience; 25(6); pp. 302-306; Jun. 1, 2002.
Fagerstrom et al.; Nicotine may relieve symptoms of Parkinson's disease; Psychopharmacology; 116(1); pp. 117-119; Sep. 16, 1994.
Food and Drug Administration; Guidance for Industry—Dissolution Testing of Immediate Release Solid Oral Dosage Forms; 17 pages; retrieved from the internet (https://www.fda.gov/downloads/drugs/guidances/ucm070237.pdf); Aug. 1997.
Gatto et al.; TC-1734: An orally active neuronal nicotinic acetylcholine receptor modulator with antidepressant, neuroprotective and long-lasting cognitive effects; CNS Drug Reviews; 10(2); pp. 147-166; Jun. 1, 2004.
Gora; Nicotine transdermal systems; The Annals of Pharmacotherapy; 27(6); pp. 742-750; Jun. 1993.
Gotti et al.; Brain nicotinic acetylcholine receptors: native subtypes and their relevance; Treands in Pharmacological Sciences; 27(9); pp. 482-491; Sep. 30, 2006.
Green et al.; An oral formulation of nicotine for release and absorption in the colon: its development and pharmacokinetics. British Journal of Clinical Pharmacology; 48(4); pp. 485-493; Oct. 1999.
He et al.; Autoradiographic analysis of dopamine receptor-stimulated [35S]GTPtS binding in rat striatum; Brain Research; 885(1); pp. 133-136; Dec. 1, 2000.
Hsu et al.; Effect of the D3 dopamine receptor partial agonist BP897 [N-[4-(4-(2-methoxyphenyl)piperazinyl) butyl]-2-napthamide] on L-3,4-dihydroxyphenylalanine-induced dyskinesias and parkinsonism in squirrel monkeys; The Journal of Pharmacology and Experimental Therapeutics. 311(2); pp. 770-777; Nov. 1, 2004.
Hukkanen et al.; Metabolism and disposition kinetics of nicotine; Pharmacological Reviews; 57(1); pp. 79-115; Mar. 1, 2005.
Ingram et al.; Preliminary observations of oral nicotine therapy for inflammatory bowel disease: an open-label phase I-II study of tolerance; Inflamm Bowel Diseases; 11(12); pp. 1092-1096; Dec. 1, 2005.
Jeyarasasingam et al.; Nitric oxide is involved in acetylcholinesterase inhibitor-induced myopathy in rats; The Journal of Pharmacology and Experimental Therapeutics; 295(1); pp. 314-320; Oct. 1, 2000.
Kulak et al.; 5-Iodo-A-85380 binds to oconotoxin Mil-sensitive nicotinic acetylcholine receptors (nAChRs) as well as 04j32* subtypes; Journal of Neurochemistry; 81(2); pp. 403-406; Apr. 1, 2002.
Kulak et al.; Declines in different pi* nicotinic receptor populations in monkey striatum after nigrostriatal damage; The Journal of Pharmacology and Experimental Therapeutics; 303(2); pp. 633-639; Nov. 1, 2002.
Kulak et al.; Loss of nicotinic receptors in monkey striatum after l-mefhyl-4-phenyl-1,2,3,6-tetrahydropyridine treatment is due to a decline in oconotoxin Mil sites; Molecular Pharmacology; 61(1); pp. 230-238; Jan. 1, 2002.
Lai et al.; Long-term nicotine treatment decreases striatal a6* nicotinic acetylcholine receptor sites and function in mice; Molecular Pharmacology; 67(5); pp. 1639-1647; May 1, 2005.
Lieber Man; Compressed tablets by direct compression; Pharmaceutical Dosage forms; vol. 1, 2nd ed.; Marcel Dekker Inc.; pp. 195-246; (year of pub. sufficiently earlier than effective US filing date and any foreign priority date) 1989.
Matta et al.; Guidelines on nicotine dose selection for in vivo research; Psychopharmacology (Berl.); 190(3); pp. 269-319; Feb. 1, 2007.
Mccallum et al,; Decrease in alpha3*/alpha6* nicotinic receptors in monkey brain after nigrostriatal damage; Molecular Pharmacology; 68(3); pp. 737-746; Sep. 2005.
Mccallum et al.; Differential regulation of mesolimbic alpha 3/alpha 6 beta 2 and aplha 4 beta 2 nicotinic acetylcholine receptor sites and function after long-term oral nicotine to monkeys; The Journal of Pharmacology and Experimental Therapeutics; 318(1); pp. 381-388; Jul. 2006.
Menzaghi et al.; Interactions between a novel cholinergic ion channel against, SIB-1765F anf L-DOPA in the reserpine model of parkinson's disease in rats; Journal of Pharmacology and Experimental Therapeutics; 280(1); pp. 393-401; Jan. 1, 1997.
National Institute of Neurological Disorders and Stroke. Parkinson's Disease: Hope Through Reasearch. 54 pages; Retrieved from the internet (https://catalog.ninds.nih.gov/pubstatic//15-139/15-139. pdf) on Jan. 15, 2018.
O'Neill et al.; The role of neuronal nicotinic acetylcholine receptors in acute and chronic neurodegeneration; Current Drug Targets—CNS and Neurological Disorders; 1(4); pp. 399-412; Aug. 1, 2002.

(56) References Cited

OTHER PUBLICATIONS

Parkinson Study Group; Levodopa and the progression of Parkinson's disease; N Engl J Med.; 351; pp. 2498-2508; Dec. 9, 2004.
Quik et al.; Chronic oral nicotine normalizes dopaminergic function and synaptic plasticity in I-methyl-4-phenyl-I,2,3,6-tetrahydropyridine-lesioned primates; The Journal ofNeuroscience; 26(17); pp. 4681-4689; Apr. 26, 2006.
Quik et al.; Chronic oral nicotine treatment protects against striatal degeneration in MPTP-treated primates; Journal of Neurochemistry; 98(6); pp. 1866-1875; Sep. 1, 2006.
Quik et al.; Differential declines in striatel nicotinic receptor subtype function after nigrostriatal damage in mice; Molecular Pharmacology; 63(5); pp. 1169-1179; May 1, 2003.
Quik et al.; Loss of a-conotoxinMII- and A85380-sensitive nicotinic receptors in Parkinson's disease striatum; Journal of Neurochemistry; 88(3); pp. 668-679; Feb. 1, 2004.
Quik et al.; Nicotine and Parkinson's disease: implications for therapy; Movement Disorders; 23(12); pp. 1641-1652; (Author Manuscript); Sep. 1, 2008.
Quik et al.; Nicotine reduces levodopa-induced dyskinesias in lesioned monkeys; Annals of neurology; 62(6); pp. 588-596; (Author Manuscript); Dec. 1, 2007.
Quik et al.; Striatal a6* nicotinic acetylcholine receptors: Potential targets for Parkinson's disease therapy; The Journal of Pharmacology and Experimental Therapeutics; 316(2); pp. 481-489; Feb. 1, 2006.
Quik et al.; Subunit composition of nicotinic receptors in monkey striatum: Effect of treatments with I-methyl-4-phenyl-I,2,3,6-tetrahydropyridine or L-DOPA; Molecular Pharmacology; 67(1); pp. 32-41; Jan. 2005.
Quik et al.; Vulnerability of 125I-a-conotoxin Mil binding sites to nigrostriatal damage in monkey; The Journal of Neuroscience; 21(15); pp. 5494-5500; Aug. 1, 2001.
Rueter et al.; ABT-089: Pharmacological properties of a neuronal nicotinic acetylcholine receptor agonist for the potential treatment of cognitive disorders; CNS Drug Reviews; 10(2); pp. 167-182; Jun. 1, 2004.
Savitt et al.; Diagnosis and treatment of Parkinson disease: molecules to medicine; The Journal of Clinical Investigation; 116(7); pp. 1744-1754; Jul. 3, 2006.
Netzel et al.; U.S. Appl. No. 15/699,382 entitled "Drug delivery methods and systems," filed Sep. 8, 2017.
Quik et al.; U.S. Appl. No. 15/611,724 entitled "Methods and compositions for reduction of side effects of therapeutic treatments," filed Jun. 1, 2017.
Azhir et al.; U.S. Appl. No. 15/659,383 entitled "Compositions and methods for treatment of symptoms in parkinson's disease patients," filed Jul. 25, 2017.
Ahlskog et al.; Frequency of levodopa-related dyskinesias and motor fluctuations as estimated from the cumulative literature; Movement Disorders; 16(3); pp. 448-458; May 1, 2001.
Chen et al.; Enhanced striatal opioid receptor-mediated G-protein activation in L-DOPA-treated dyskinetic monkeys; Neuroscience; 132(2); pp. 409-420; Dec. 31, 2005.
Di Monte et al.; Relationship among nigrostriatal denervation, parkinsonism, and dyskinesias in the MPTP primate model; Movement Disorders; 15(3); pp. 459-466; May 1, 2000.
Domino et al.; Nicotine alone and in combination with L-DOPA methyl ester or the D2 agonist N-0923 in MPTP-induced chronic hemiparkinsonian monkeys; Experimental Neurology; 158(2); pp. 414-421; Aug. 31, 1999.
Ebersbach et al.; Worsening of motor performance in patients with Parkinson's disease following transdermal nicotine administration; Movement Disorders; 14(6); pp. 1011-1013; Nov. 1, 1999.
He et al; Autoradiographic analysis of N-methyl-D-aspartate receptor binding in monkey brain: Effects of I-methyl-4-phenyl-I,2,3,6-tetrahyriropyridine andleyodcpa treatment; Neuroscience; 99(4); pp. 697-704; Aug. 23, 2000.

Jeyarasasingam et al.; Stimulation of non-o7 nicotinic receptors partially protects dopaminergic neurons from I-methyl-4-phenylpyridinium-induced toxicity in culture; Neuroscience; 109(2); pp. 275-285; Jan. 28, 2002.
Jeyarasasingam et al.; Tacrine, a reversible acetylcholinesterase inhibitor, induces myopathy; Neuroreport; 11(6); pp. 1173-1176; Apr. 27, 2000.
Kelton et al.; The effects of nicotine on Parkinson's disease; Brain Cognition; 43(1-3); pp. 274-282; Jun. 2000.
Lai et al.; Selective recovery of striatal 125I-a-conotoxinMII nicotinic receptors after nigrostriatal damage in monkeys; Neuroscience; 127(2); pp. 399-408; Dec. 31, 2004.
Langston et al.; Investigating levodopa-induced dyskinesias in the parkinsonian primate; Annals of Neurology; 47(4 Suppl 1); pp. S79-S88; Apr. 2000.
Mccallum et al.; Compensation in pre-synaptic dopaminergic function following nigrostriatal damage in primates; Journal of Neurochemistry; 96(4); pp. 960-972; Feb. 1, 2006.
Mccallum et al.; Increases in aplha 4* but not aplha3*/alpha6* nicotinic receptor sites and function in the primate striatum following chronic oral nicotine treatment; Journal of Neurochemistry; 96(4); pp. 1028-1041; Feb. 2006.
Meredith et al.; Behavioral models of Parkinson's disease in rodents: a new look at an old problem; Movement Disorders; 21(10); pp. 1595-1606; Oct. 1, 2006.
Meshul et al.; Nicotine Affects Striatal Glutamatergic Function in 6-OHDA Lesioned Rats; Advanced in behavioural Biology. Basal Ganglia VI.; Springer, Boston, MA.; vol. 54; pp. 589-598; (year of pub. sufficiently earlier than effective US filing date and any foreign priority date) 2002.
Meshul et al.; Nicotine alters striatal glutamate function and decreases the apomorphine-induced contralateral rotations in 6-OHDA-lesioned rats; Experimental Neurology; 175(1); pp. 257-274; May 31, 2002.
Olanow; The scientific basis for the current treatment of Parkinson's disease; Annu. Rev. Med.; 55; pp. 41-60; Feb. 18, 2004.
Petzinger et al.; Reliability and validity of a new global dyskinesia rating scale in the MPTP-lesioned non-human primate; Movement Disorders; 16(2); pp. 202-207; Mar. 1, 2001.
Quik et al.; Differential alterations in nicotinic receptor a6 and /33 subunit messenger RNAs in monkey substantia nigra after nigrostriatal degeneration; Neuroscience; 100(1); pp. 63-72; Sep. 7, 2000.
Quik et al.; Differential nicotinic receptor expression in monkey basal ganglia: Effects of nigrostriatal damage; Neuroscience; 112(3); pp. 619-630; Jul. 5, 2002.
Quik et al.; Expression of D3 receptor messenger RNA and binding sites in monkey striatum and substantia nigra after nigrostriatal degeneration: Effect of levodopa treatment.;Neuroscience; 98(2); pp. 263-273; Jun. 30, 2000.
Quik et al.; Increases in striatal preproenkephalin gene expression are associated with nigrostriatal damage but not L-DOPA-induced dyskinesias in the squirrel monkey; Neuroscience; 113(1); pp. 213-220; Aug. 2, 2002.
Quik et al.; Localization of nicotinic receptor subunit mRNAs in monkey brain by in situ hybridization; The Journal of Comparative Neurology; 425(1); pp. 58-69; Sep. 11, 2000.
Quik et al.; Nicotine administration reduces striatal MPP+ levels in mice; Brain Research; 917(2); pp. 219-224; Nov. 2, 2001.
Quik et al.; Nicotine neuroprotection against nigrostriatal damage: importance of the animal model; Trends in Pharmacological sciences; 28(5); pp. 229-235; May 31, 2007.
Quik et al.; Nicotinic receptors and Parkinson's disease; European Journal of Pharmacology; 393(1); pp. 223-230; Mar. 30, 2000.
Samii et al.; Parkinson's disease; The Lancet; 363(9423); pp. 1783-1793; May 29, 2004.
Schapira; Disease modification in Parkinson's disease; The Lancet Neurology; 3(6); pp. 362-368; Jun. 30, 2004.
Schneider et al.; Effects of SIB-1508Y, a novel neuronal nictonic acetylcholine receptor agonist, on motor behavior in parkinsonian monkeys; Movement Disorders; 13(4); pp. 637-642; Jul. 1, 1998.
Schneider et et; Effects of the nicotinic acetylcholine receptor agonist SIB-1508Y on object retrieval performance in MPTP-

(56) References Cited

OTHER PUBLICATIONS treated monkeys: Comparison with levodopa treatment; Annals of Neurology; 43(3); pp. 311-317; Mar. 1, 1998.
Schober et al.; Classic toxin-induced animal models of Parkinson's disease: 6-OHDA and MPTP; Cell and Tissue Research; 318(1); pp. 215-224; Oct. 1, 2004.
Stocchi et al.; Motor fluctuations in levodopa treatment: clinical pharmacology; European Neurology; 36(Suppl 1); pp. 38-42; Jan. 1996.
Togasaki et al.; Dyskinesias in normal squirrel monkeys induced by nomifensine and levodopa; Neuropharmacology; 48(3); pp. 398-405; Mar. 31, 2005.
Togasaki et al.; Levodopa induces dyskinesias in normal squirrel monkeys; Annals of Neurology; 50(2); pp. 254-257; Aug. 1, 2001.
Togasaki et al.; The Webcam system: A simple, automated, computer-based video system for quantitative measurement of movement of nonhuman primates; Journal of Neuroscience Methods; 145(1); pp. 159-166; Jun. 30, 2005.
Vieregge et al.; Transdermal nicotine in PD: A randomized, double-blind, placebo-controlled study; Neurology; 57(6); pp. 1032-1035; Sep. 25, 2001.
Westman et al.; Oral nicotine solution for smoking cessation: a pilot tolerability study; Nicotine and Tobacco Research; 3(4); pp. 391-396; Nov. 1, 2001.
Balfour et al.; Pharmacology of nicotine and its therapeutic use in smoking cessation and neurodegenerative disorders; Pharmacology and Therapeutics; 72(1); pp. 51-81; Jan. 1, 1996.
Benowitz et al.; Stable isotope studies of nicotine kinetics and bioavailability; Clin Pharm and Ther; 49(3); pp. 270-277; Mar. 1991.
Hurley; Growing list of positive effects of nicotine seen in neurodegenerative disorders; Neurology Today; 12(2); pp. 37-38; Jan. 19, 2012.
Janson et al.; Chronic nicotine treatment counteracts dopamine D2 receptor upregulation induced by a partial meso-diencephalic hemitransection in the rat; Brain Res.; 655(1-2); pp. 25-32; Aug. 29, 1994.
Kumar et al.; Levodopa-dyskinesia incidence by age of Parkinson's disease onset; Movement disorders; 20(3); pp. 342-344; Mar. 2005.
Lee et al.; A comprehensive review of opioid-induced hyperalgesia; Pain Physician; 14; pp. 145-161; Mar. 2011.
Newhouse et al.; Nicotine treatment of mild cognitive impairment: a 6-month double-blind pilot clinical trial; Neurology; 78(2); pp. 91-101; Jan. 10, 2012.
Quik et al.; Nicotine as a potential neuroprotective agent for Parkinson's disease; Movement disorders; 27(8); pp. 947-957; Jul. 1, 2012.
United States of America VA/DoD; Tapering and discontinuing opioids; 2 pages; retrieved from the internet (http://www.healthquality.va.gov/guidelines/Pain/cot/OpioidTaperingFactSheet23May2013v1.pdf); on Sep. 1, 2016.
U.S. Department of Health and Human Services, Food and Drug Administration, Center for Drug Evaluation and Research (CDER); Guidance for industry: Abuse-deterrent opioids—Evaluation and labeling; 24 pages; retrieved from the internet (http://www.fda.gov/downloads/drugs/guidancecomplainceregulatoryinformation/guidances/ucm344743.pdf); Jan. 2013.
Wermuth et al.; Glossary of terms used in medicinal chemistry Pure & Appl. Chem., vol. 70(5); 1129-1143; 1998 AC recommendations 1998); Pure and Applied Chemistry; 70(5); pp. 1129-1143; Jan. 1998.
Zubieta et al.; Placebo effects mediated by endogenous opioid activity on mu-opioid receptors; 25(34); pp. 7754-7762; Aug. 24, 2005.

\* cited by examiner

FIG. 9A
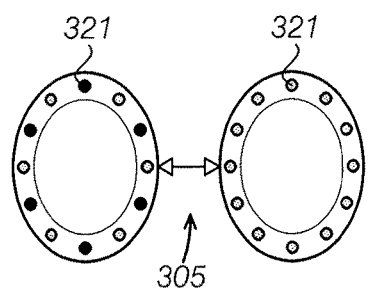
FIG. 9B
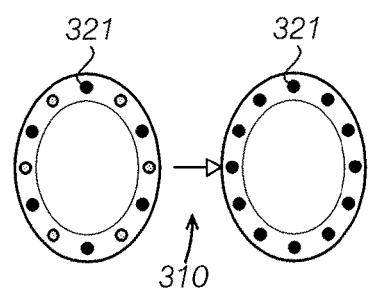
FIG. 9C
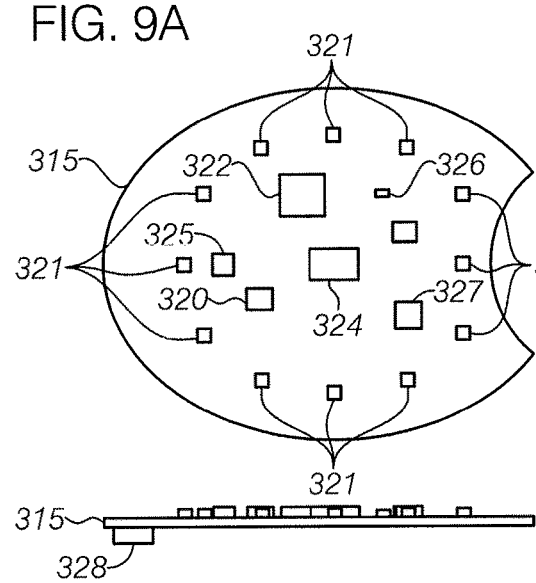
FIG. 9D
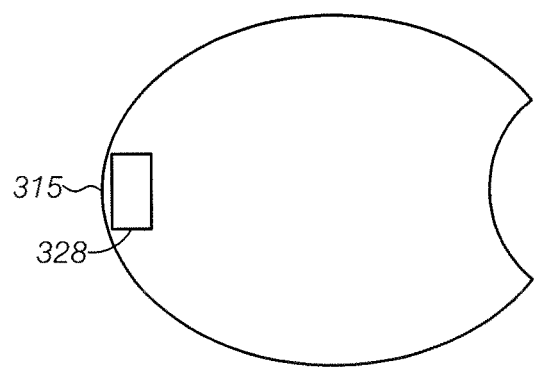
FIG. 9E
FIG. 9F

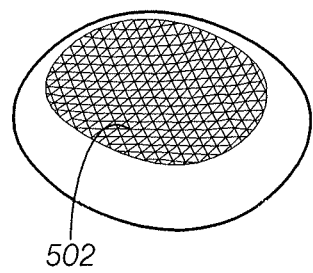
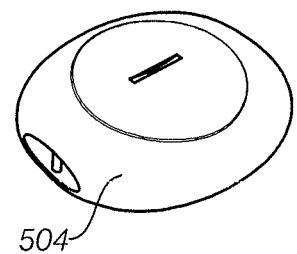
FIG. 11A  FIG. 11B
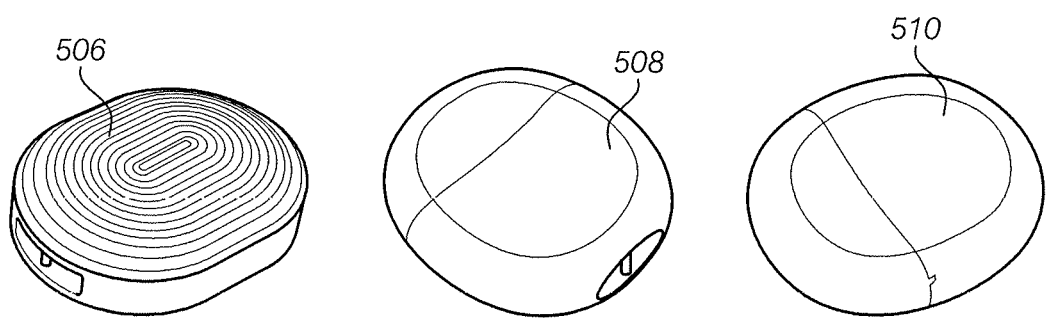
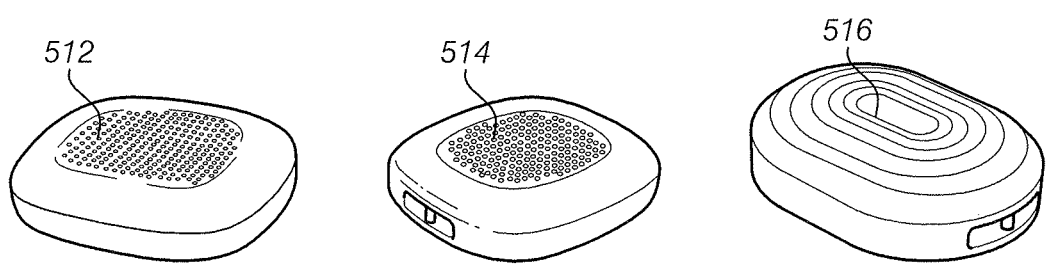
FIG. 11C

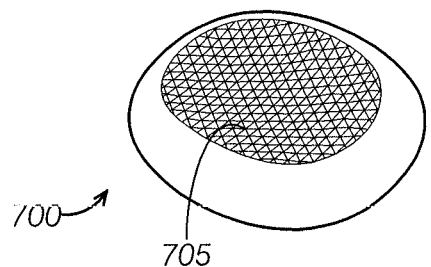
FIG. 13A
| NUMBER OF TAPS | DURATION BETWEEN TAPS | INTENSITY OF CRAVING |
|---|---|---|
| 1 | N/A | NEUTRAL / DEFAULT |
| 2-4 | LESS THAN 300ms | ELEVATED |
| 4+ | LESS THAN 150ms | HIGH |
FIG. 13B
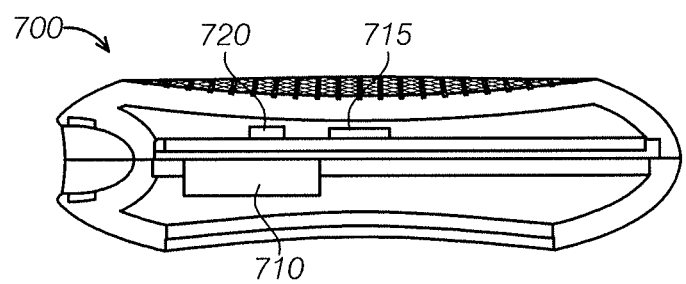
FIG. 13C

| NUMBER OF TAPS | DURATION BETWEEN TAPS | INTENSITY OF CRAVING | SIZE OF CIRCLE THAT REPRESENTS ACTIVITY |
|---|---|---|---|
| 1 | N/A | NEUTRAL/DEFAULT | • |
| 2-4 | LESS THAN 300ms | ELEVATED | ● |
| 4+ | LESS THAN 150ms | HIGH | ⬤ |

CRAVING INPUT AND SUPPORT SYSTEM

CROSS REFERENCE TO RELATED APPLICATIONS

The present application claims the benefit of U.S. Provisional Application No. 62/132,436 filed on Mar. 12, 2015, the disclosure of which is herein incorporated by reference in its entirety.

INCORPORATION BY REFERENCE

All publications and patent applications mentioned in this specification are incorporated herein by reference in their entirety to the same extent as if each individual publication or patent application was specifically and individually indicated to be incorporated by reference.

BACKGROUND

Communication devices to assist users change habitual behavior are known in the prior art. For example, U.S. Pat. No. 5,596,994 describes an interactive behavior modification system that provides motivational messages to a user and obtains information from the user using a computer, personal digital assistant or other personal communication system. In one embodiment, the device asks the user questions, and the user may depress buttons to select answers. Motivational or behavioral information may be sent to the user via the device.

U.S. Pat. No. 6,567,785 describes a behavior modification device that asks the user whether unwanted behavior has occurred within an earlier time period. The frequency and timing of the prompt signal depends on the response to the previous prompt; future prompts come sooner and more frequently if unwanted behavior has occurred. The system cannot receive unprompted input from the user, such as by indicating when the user has a desire or craving for the undesired behavior, and it therefore has no way to respond to such an unprompted indication from the user.

There are applications that run on a smartphone that allow users to track cravings and that provide coaching tips for coping with such cravings. Smokers are able to record how often they overcome cravings and see visual renderings of their progress on the mobile application itself. The smartphone application must be used on a smartphone, of course, and therefore lacks an easy and discreet form factor for an input mechanism to identify cravings.

U.S. Patent Publ. No. 2014/0207048 describes a drug delivery device that includes a data collection application into which the user can input a craving for, e.g., a cigarette. In addition to providing nicotine to help satisfy the craving, the system can respond with a message via text or phone encouraging the user to maintain his or her conviction to the treatment protocol.

FIELD

The present application relates generally to the field of addiction treatment and craving support. The cravings can be associated with drugs, bioactive agents, other pharmaceutical substances, food, TV, stress, OCD-type behaviors, and other behaviors that can induce cravings.

BACKGROUND

Successfully quitting an addiction can involve weaning oneself off of the drug and/or modifying psychological and habitual behaviors associated with the addiction or behavior. Cravings associated with a physical drug dependency and/or psychological and habitual behaviors associated with the addiction can result in a relapse. Cravings can occur at set times or can be triggered by external events. Typically the cravings for the specific addictive substance and/or the addictive behavior can last on the order of several minutes and then pass. Improved methods and devices are desired to provide support for the user or patient to handle the periodic cravings with the goal of decreasing instances of relapse and to improve the user's overall success at quitting the addiction.

SUMMARY OF THE DISCLOSURE

The present invention relates generally to systems and methods for providing support to a user of a device to handle cravings.

In general, in one embodiment, a craving control device includes a housing, a craving input actuator supported by the housing, the craving input actuator being configured to obtain information from a user pertaining to a timing, frequency, or intensity of a craving, a wireless communicator supported by the housing, a controller operatively connected to the craving input actuator and the wireless communicator to communicate craving timing, frequency, or intensity information received by the craving input actuator via the wireless communicator to a device external to the housing.

This and other embodiments can include one or more of the following features. The housing can be sized and configured to be enclosed in the user's hand. The housing can be sized and configured to be placed in a pocket of the user's clothing. The housing can be sized and configured to be worn on the user's clothing. The craving control device can further include a distraction feature adapted to distract the user during a craving episode. The distraction feature can be a textured area on an exterior surface of the housing. The distraction feature can be a user-movable element supported by the housing. The distraction feature can be a timer marking an expected duration of the craving episode. The timer can start with actuation of the craving input actuator. The timer can include a visual display configured to change during the expected duration of the craving episode. The visual display can include a plurality of lights. The timer can include a vibration source operable by the controller to vibrate for the expected duration of the craving episode. The controller can be configured to operate the vibration source to vibrate with an intensity that varies during the expected duration of the craving episode. The craving control device can further include a user parameter sensor supported by the housing and adapted to obtain user parameter information relevant to the craving, the controller can be operatively connected to the user parameter sensor to communicate user parameter information sensed by the sensor via the wireless communicator to the device external to the housing. The craving control device can further include an environmental parameter sensor supported by the housing and adapted to obtain environmental information relevant to the craving, the controller can be operatively connected to the environmental parameter sensor to communicate environmental parameter information sensed by the sensor via the wireless communicator to the device external to the housing. The craving control device can further include a breath sensor and a display supported by the housing, the controller can be operatively connected to the display to provide a target breathing pattern for the user and to the breath sensor to measure a breathing pattern of the user. The craving control device can further include the external device, the external device can include a personal communication device which can have a processor programmed to electronically send a message to a support contact provided by the user. The craving control device can further include the external device, the external device can include a personal communication device which can have a processor programmed to provide craving support to the user in response to craving information from the craving input actuator. The processor of the craving control device can further be programmed to provide the craving support proactively to the user based on a past information from the user pertaining to craving occurrence and craving intensity. The craving control device can further include a user parameter sensor, the personal communication device processor can be further programmed to provide craving support to the user in response to a user parameter sensed by the sensor. The user parameter sensor can include one or more of a: humidity sensor, breath sensor, nicotine sensor, carbon monoxide sensor, carbon dioxide sensor, oxygen sensor, inertia sensor, electrocardiogram (ECG) lead, electromyography (EMG) lead, accelerometer, blood pressure sensor, galvanic skin response sensor, temperature sensor, and heart rate sensor. The craving control device can further include an environmental parameter sensor, the personal communication device processor being further programmed to provide craving support to the user in response to environmental parameter information sensed by the sensor. The environmental parameter sensor can include an ambient light sensor, ultraviolet light sensor, air pressure sensor, environmental pollutant sensor, or a temperature sensor. The controller can further be configured to determine the intensity of the craving based on a pattern received by the input actuator.

In general, in one embodiment, a method of receiving a craving input from a user including receiving information from the user pertaining to a craving occurrence and an intensity of a craving with a craving control device including a housing and a craving input actuator supported by the housing, the information from the user pertaining to the craving occurrence and craving intensity of the craving received through the craving input actuator; and wirelessly communicating craving occurrence and craving intensity information received by the craving input actuator to a device external to the housing.

This and other embodiments can include one or more of the following features. The method can further include providing a distraction to the user in response to the craving occurrence and craving intensity information with a distraction feature that is part of the craving control device. The distraction feature can be a textured area on an exterior surface of the housing. The distraction feature can be a user-movable element supported by the housing. The distraction feature can be a timer marking an expected duration of the craving episode, can further include starting the timer after actuation of the craving input actuator. The method can further include providing a visual display with the timer that changes during the expected duration of the craving episode. Providing the visual display can include providing a plurality of lights. The timer can include a vibration source operable by the controller and further include vibrating the vibration source for the expected duration of the craving episode. The method can further include varying an intensity of the vibration source during the expected duration of the craving episode. The method can further include receiving a user parameter information relevant to the craving with a user parameter sensor supported by the housing and wirelessly transmitting data corresponding to the user parameter information to the device external to the housing. The method can further include receiving an environmental parameter information relevant to the craving with an environmental parameter sensor supported by the housing and wirelessly transmitting data corresponding to the environmental parameter information to the device external to the housing. The method can further include receiving breathing parameter information relevant to the craving from the user with a breath sensor supported by the housing and providing a target breathing pattern for the user with a display supported by the housing. The method can further include providing a craving support to the user in response to craving information from the craving input actuator with the external device. The method can further include receiving information from a user parameter sensor supported by the housing and providing a craving support to the user based on a user parameter sensed by the user parameter sensor. The user parameter sensor can include one or more of a: humidity sensor, breath sensor, nicotine sensor, carbon monoxide sensor, carbon dioxide sensor, oxygen sensor, inertia sensor, electrocardiogram (ECG) lead, electromyography (EMG) lead, accelerometer, blood pressure sensor, galvanic skin response sensor, temperature sensor, and heart rate sensor. The method can further include receiving information from an environmental parameter sensor supported by the housing and providing a craving support to the user based on the environmental parameter sensed by the environmental parameter sensor. The environmental parameter sensor can include an ambient light sensor, ultraviolet light sensor, air pressure sensor, environmental pollutant sensor, or a temperature sensor. The housing can be sized and configured to be enclosed in the user's hand. The housing can be sized and configured to be placed in a pocket of the user's clothing. The external device can include a personal communication device including a display and further including providing instructions to the user to modify a breathing pattern of the user with the display of the personal communication device. The external device can include a personal communication device including a display and further including providing information to the user with the display of the personal communication device relating to the timing and intensity of the cravings. The method can further include determining the intensity of the craving based on a pattern received by the input actuator. The external device can include a personal communication device and further including electronically sending a message to a support contact provided by the user upon receiving information from the user pertaining to the occurrence and intensity of the craving. The method can further include providing a distraction to the user proactively based on a past information from the user pertaining to craving occurrence and craving intensity.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 9A illustrates a user breathing onto an embodiment of a craving control device. FIGS. 9B and 9C illustrate schematics of different light patterns displayed by a craving control device. FIG. 9D illustrates a top view of an embodiment of a printed circuit board with sensors that can be used in the craving control devices described herein. FIG. 9E illustrates a side view of an embodiment of a printed circuit board with sensors that can be used in the craving control devices described herein. FIG. 9F illustrates a bottom view of an embodiment of a printed circuit board with sensors that can be used in the craving control devices described herein.

FIGS. 11A-11C illustrate multiple different surfaces and textures that can be used in embodiments of craving control devices.

FIG. 13A illustrates a top view of an embodiment of a craving control device. FIG. 13B illustrates a chart showing an embodiment correlating button taps to craving intensity. FIG. 13C illustrates a cross-sectional view of an embodiment of a craving control device.

DETAILED DESCRIPTION

Figure 1A:
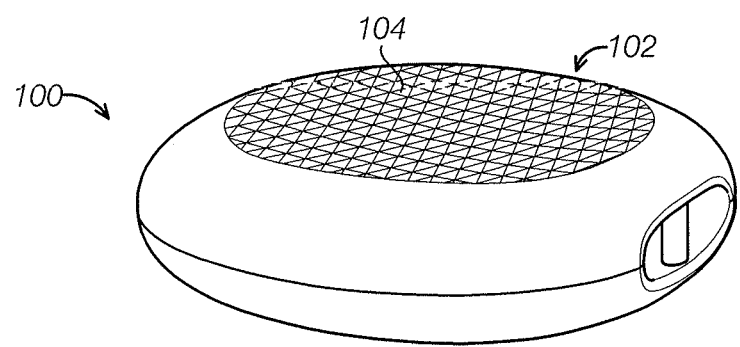
FIGS. 1A and 1B illustrate a top view and a bottom view, respectively, of a craving control device in accordance with some embodiments.

Individuals experiencing cravings they wish to resist (e.g., nicotine cravings) would benefit from a discreet and effective way to communicate a craving and receive support to resist the craving. The prior art has not provided a device and system to do so. The craving control device is designed so that the physical device is hidden from others and the way that it is interacted with can be hidden and discreet. The craving control device can provide support to the user during a craving episode or proactively prior to a craving episode to reduce the likelihood of the user relapsing. The craving control devices described herein can increase the overall success for the user to quit the addictive activity.

Craving control device are described herein. The craving control devices can include a housing and a craving input actuator supported by the housing. The craving input actuator can be configured to obtain information from a user pertaining to a timing, frequency, or intensity of a craving. The user can press a surface of the housing to actuate the craving input actuator. The craving control device can include a wireless communicator supported by the housing. The craving control device can include a controller operatively connected to the craving input actuator and the wireless communicator to communicate craving timing, frequency, or intensity information received by the craving input actuator via the wireless communicator to a device external to the housing.

One embodiment of the invention provides a drug delivery system for, e.g., delivering nicotine transdermally and includes a mechanism for activation by a user to identify a craving experienced by the user. The mechanism may be, e.g., a button on a transdermal delivery device such as that disclosed in U.S. Patent Publ. No. 2014/0207048. In some embodiments, the system will record the incidence and duration of the cravings. The system may also give the user tactile, visual and/or auditory feedback related to and during craving episodes to help the user cope with craving-related anxiety and to provide encouragement to the user to overcome the craving. The system may also send data, such as that of a cigarette craving, duration of a craving, and result of the craving (e.g., smoking a cigarette or overcoming the craving), to a companion mobile app in a nearby smartphone for behavioral support and predictive modeling.

The craving control device can have a discrete size and shape. The housing can be sized and configured to be enclosed in the user's hand. The housing can be sized and configured to be placed in a pocket of the user's clothing. The housing can be sized and configured to be worn on the user's clothing.

The craving control device can provide craving support and behavioral support. The support can be provided in anticipation of a craving or upon actuation of the craving input actuator on the craving control device.

The craving control device can include a distraction feature adapted to distract the user during a craving episode. In some embodiments the distraction feature can be a textured area on an exterior surface of the housing. In some embodiments the distraction feature can be a user-movable element supported by the housing. The textured surface and user-movable element can both function as a distraction to the user by redirecting physical habits to reduce cravings. In the example of nicotine dependency the distraction feature can provide the user something to do with their hands to distract them from the hand-to-mouth smoking gesture. The user can rub the textured surface and/or move the user-movable element to distract from the craving episode. The craving input device can also gather user data via the movement of the user-movable element and the use of the textured surface to categorize or quantify the craving episode, such as the craving intensity.

In some embodiments the distraction feature can be a timer marking an expected duration of the craving episode. The timer can distract the user from the craving episode. The timer can start with actuation of the craving input actuator. In some embodiments the timer can include a visual display configured to change during the expected duration of the craving episode. The visual display can include a plurality of lights. In some embodiments the timer can include a vibration source operable by the controller to vibrate for the expected duration of the craving episode. The controller can be configured to operate the vibration source to vibrate with an intensity that varies during the expected duration of the craving episode. The tinier feedback mode (e.g. visual through the display or tactile through the vibration source) can be automatically selected by the craving control device. For example, an ambient light sensor on the device can determine the ambient light conditions. If a dark environment is detected, such as the device is enclosed in the hand of the user, then tactile feedback can be selected and initiated. If a light environment is detected then the visual feedback can be initiated. The length of the timer can be selected based on a typical craving length of about two minutes. In some embodiments the timer duration can be set by the user or determined by the system based on the user information. The user can let the timer go through the entire 2 minutes or they can stop the timer, which then lets the system know that the craving was overcome earlier than the 2 minutes. The user can also input whether they overcome the craving using the craving control device or the smartphone companion application.

In some embodiments the vibration source and/or the visual display can be used to convey information to the user. The visual display can be represented as a circle of lights that rotates to indicate time, pulses to indicate intensity, and changes color to indicate type of content. The vibration source can be configured to generate a series of patterns that can represent specific information, such as a timer, intensity, and specific information. The users can also customize the display and vibrational patterns for the timer through the companion smartphone application.

The craving control device can include a variety of different sensors, such as user parameter sensors and environmental sensors. The sensors can be supported by the housing and a controller in the craving control device can be operatively connected to the sensor to communicate sensor information sensed by the sensor via the wireless communicator to a device external to the housing. The sensors can be supported on a printed circuit board (PCB) within the housing of the craving control device or in electrical communication with a processor on the PCB.

The user parameter sensor can include one or more of a: humidity sensor, breath sensor, nicotine sensor, carbon monoxide sensor, carbon dioxide sensor, oxygen sensor, inertia sensor, electrocardiogram (ECG) lead, electromyography (EMG) lead, accelerometer, blood pressure sensor, galvanic skin response sensor, temperature sensor, and heart rate sensor. In the example of the ECG lead or EMG lead, sensors can be used that adhere to the skin of the user and that are in electrical communication with the processor to relay signals sensed by the ECG lead/EMG lead.

The environmental parameter sensor can include one or more of: an ambient light sensor, ultraviolet light sensor, air pressure sensor, environmental pollutant sensor, or a temperature sensor.

In some embodiments the craving control device can include a breath sensor and a display supported by the housing. The breath sensor can sense the user's breathing pattern and the display of the craving control device can provide a target breathing pattern for the user. Instructions can also, or in the alternative, be provided to the user to modify a breathing pattern of the user with a display of a personal communication device.

The controller can be configured to determine the intensity of the craving based on a pattern received by the craving input actuator, such as the number of times the craving input actuator is actuated and a time between actuations of the craving input actuator. The severity and mood of a craving can he assigned based on the pattern of actuating the input actuator. A software algorithm calculates the severity based on frequency and duration of presses over a duration of time. For example, if the button is pressed multiple times in a short amount of time (seconds) or, alternatively, if the button is press firmly vs. gently, then the system can register the craving as being more severe. The level of severity of the craving can be visualized in a display.

The external device can include a personal communication device having a processor. The processor can be programmed to electronically send a message to a support contact provided by the user. The processor can be programmed to provide craving support to the user in response to craving information from the craving input actuator. The processor in the personal communication device can be programmed to provide a craving support proactively to the user based on a user history data or user information like the occurrence and intensity of a craving. The processor of the personal communication device can be configured to provide information to the user with the display of the personal communication device relating to the timing and intensity of the cravings.

In some embodiments, the craving input mechanism may be in a structure independent of a drug delivery device. In such embodiments, the system may include a craving input mechanism supported on a wearable device such as a bracelet, broach or pendant. The user may activate the craving input mechanism to identify a craving incident, and the system may record the incidence and duration of the cravings. The system may also give the user tactile (e.g., via haptic feedback in vibrational patterns against the user's body), visual and/or auditory feedback (e.g., LED displays and audible chimes) related to and during craving episodes to help the user cope with craving-related anxiety and to provide encouragement to the user to overcome the craving. The system may also send data, such as the of a cigarette craving, duration of a craving, and result of the craving (e.g., smoking a cigarette), to a companion mobile app in a nearby smartphone for behavioral support and predictive modeling. The system may be used to address cravings and addictive behavior attributed to cigarette smoking, food cravings; sugar cravings; alcohol cravings; marijuana cravings; nicotine cravings; gambling cravings;

sexual cravings; and other destructive compulsive behaviors. Other form factors of the device include a wristband, an armband, an anklet, a necklace, a ring, an earring, and an adhesive-attached pod. The device may also be a stand-alone system not worn on the body. The device could include multiple sensors and functions that support the system's overall pursuit of improved health and wellbeing. These sensors and functions could include but are not limited to: accelerometers, heart rate monitors, blood pressure monitors, skin temperature monitors, haptic vibration patterns, LED displays, and auditory signals. This functionality may also be combined with a transdermal drug delivery device, such as that disclosed in U.S. Patent Publ. No. 2014/0207048.

In some embodiments, the system may be used to record the beginning of a craving episode, the end of a craving episode, the duration of a craving episode, and/or the result of a craving episode (i.e., whether or not the user succumbed to the craving). The craving input mechanism may be, e.g., button(s), lever(s), a surface that registers a gesture such as a swipe, a press, a tap, and/or a pinch, and/or a speaker for an audio recording.

In some embodiments, the system may include one or more of the following:

a backend subsystem that stores data in a secure and confidential manner and includes an algorithm-driven predictive modeling engine that analyzes data from the craving input mechanism a mobile application to predict cravings, trend historical cravings data, and trigger proactive tailored messages to help users cope with cravings a mobile device capable of receiving data about the craving event, whether via a wireless connection, a wired connection or both a computer capable of receiving data about the craving event, whether via a wireless connection, a wired connection or both a large, multi-user application, which is capable of receiving data about the craving event, whether via a wireless connection or a wired connection, or both.

These and other features enable the system of this invention to capture and record craving events discretely and easily to aid the user with understanding their unique and individual craving patterns and data related to succumbing and/or overcoming the cravings. Furthermore, the data captured can he transferred to a larger system to harness unique processing capabilities of a larger ecosystem. The data that is captured in each recording includes but is not limited to: time of craving, length of craving from start of episode to end of episode, and result of the craving.

In some embodiments, each time the user actuates the craving input mechanism to indicate a craving episode, the system initiates a built-in timer, which signals via vibration, sound or visual display, the start and end of the craving episode to the user. As most craving episodes last only a few minutes, the built-in timer will signal to the user when the craving should be ending. After the timer indicates the completion of the craving episode, the user will receive tactile, visual or auditory feedback from the system that the craving episode has passed. Users benefit from knowing that each craving episode lasts a fixed duration with a definitive end.

In some embodiments, the system includes sensors and built-in functionality to provide feedback to the user regarding each craving episode and series of episodes. The feedback may include: (1) haptic vibrational patterns felt against the body that are designed to soothe the User in the moment of the craving and provide information about the craving; (2) visual displays on the device (lights, animations, text, etc.) to provide the user with data regarding the cravings and encouragement to cope with cravings; and/or (3) auditory signals such as chimes and beeps to signal craving events and provide information about the cravings to the user. The feedback is triggered via algorithms embedded within the system that leverage the user's data collected by the craving input mechanism itself.

In some embodiments, the system includes a mechanism configured to provide physical vibrational patterns felt against the body to the user during a user-reported craving episode, as entered by the user via the craving input mechanism. The craving therapy could take the form of, e.g., a combination of vibrational/haptic patterns felt against the user's body along with visual and auditory signals. The patterns emitted by the device are intended to provide therapeutic, calming benefit to the user to help him/her cope with the craving, and associated feelings of anxiety, in the moment the craving is occurring.

Some embodiments of the invention includes a craving calculator, i.e., a robust set of analytics and predictive algorithms that harness data collected through the craving input mechanism as well as from other applications, such as a complementary mobile application or third party mobile tools, and then analyze and compute both craving data input by the user and data from the user's ecosystem (e.g., data collected by other apps running on a smartphone/desktop system) to educate and inform the user about his/her past and future craving episodes. Example of data that can be analyzed includes: the number of cravings, severity of cravings, mood, physical activity, location during times of cravings, etc. This innovation allows a user to view historical patterns of his/her cravings in context of their lives as well as predictive data for when future cravings may occur.

Figure 1B:
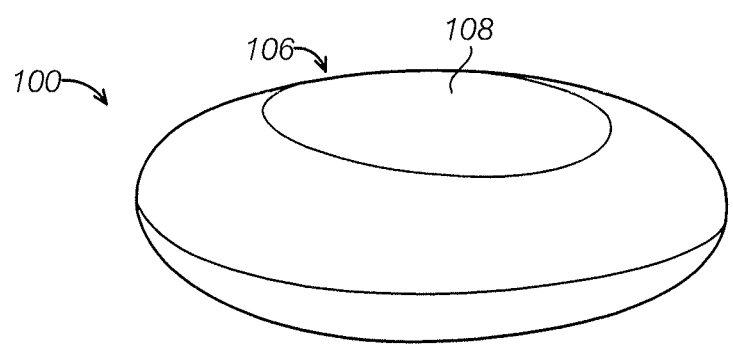

FIGS. 1A and 1B illustrate a top view and a bottom view, respectively, of a craving control device 100 in accordance with some embodiments. The craving control device 100 includes a housing with a first surface 102 and a second surface 106 on an opposing side of the housing from the first surface 102. The first surface 102 includes a textured area 104 that can serve as a distraction feature. The first surface 102 can be flexibly such that the user can press the surface to actuate one or more actuators or buttons internal to the housing of the crave control device 100. The first surface 102 is illustrated with a concave configuration. The second surface 106 is illustrated with a smooth texture 108.

Figure 2A:
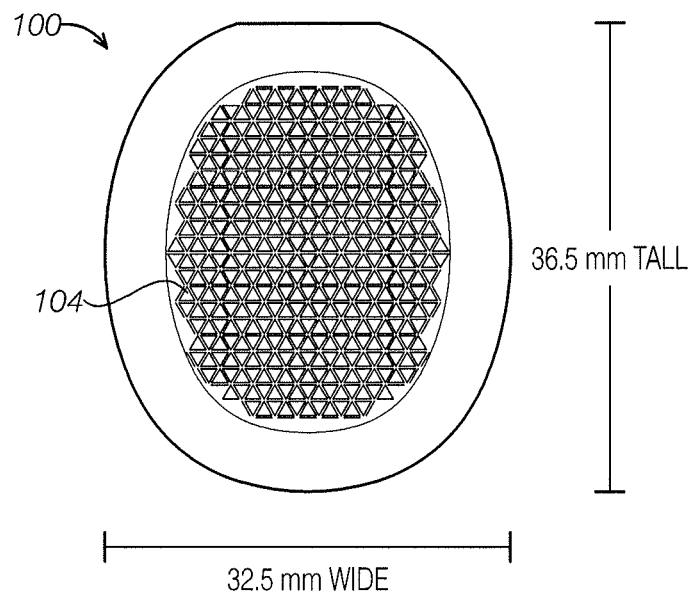
FIGS. 2A-2C illustrate a top view and two side views, respectively of a craving control device in accordance with some embodiments.
Figure 2B:
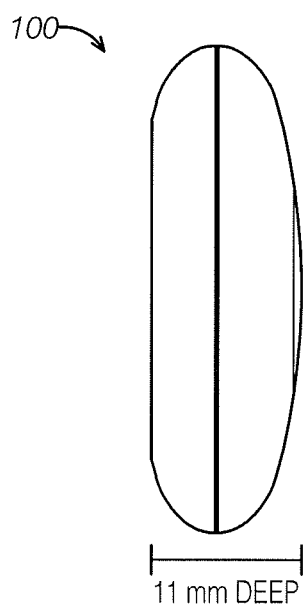
Figure 2C:
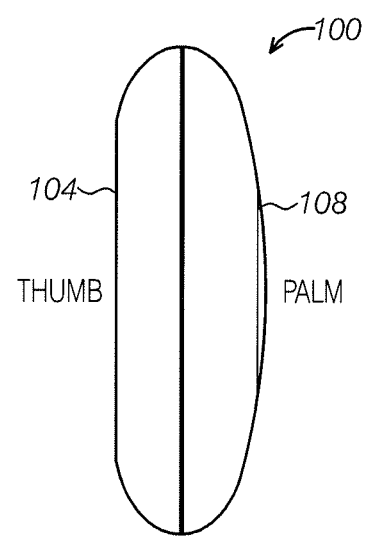

FIGS. 2A-2C illustrate a top view and two side views, respectively of a craving control device 100 in accordance with some embodiments. The illustrated craving control device 100 is designed such that it can be used discreetly. The illustrated craving control device 100 is sized such that it can be discreetly held in the user's hand, placed in a pocket, or used such that it others do not know the user is holding or using the device. The craving control device 100 is illustrated as 36.5 mm tall, 32.5 mm wide, and 11 mm deep. The illustrated craving control device 100 includes matte finish on a portion of the first surface 102 that can provide an easier hand grip to help prevent dropping the device. A smooth finish, such as a high-polish smooth finish can be provided on the second surface 108 to allow for easier insertion into a pocket. The smooth finish of the second surface 108 and illustrated convex curved shape can improve the comfortable engagement with the palm of the user. The first surface 102 and textured area 104 have a concave curved shape that conforms to the thumb to allow the user to push the surface with the thumb to actuate a craving input actuator within the device 100 and to rub the first surface 102 and the textured area 104 to receive a distraction when experiencing a craving.

Figure 3:
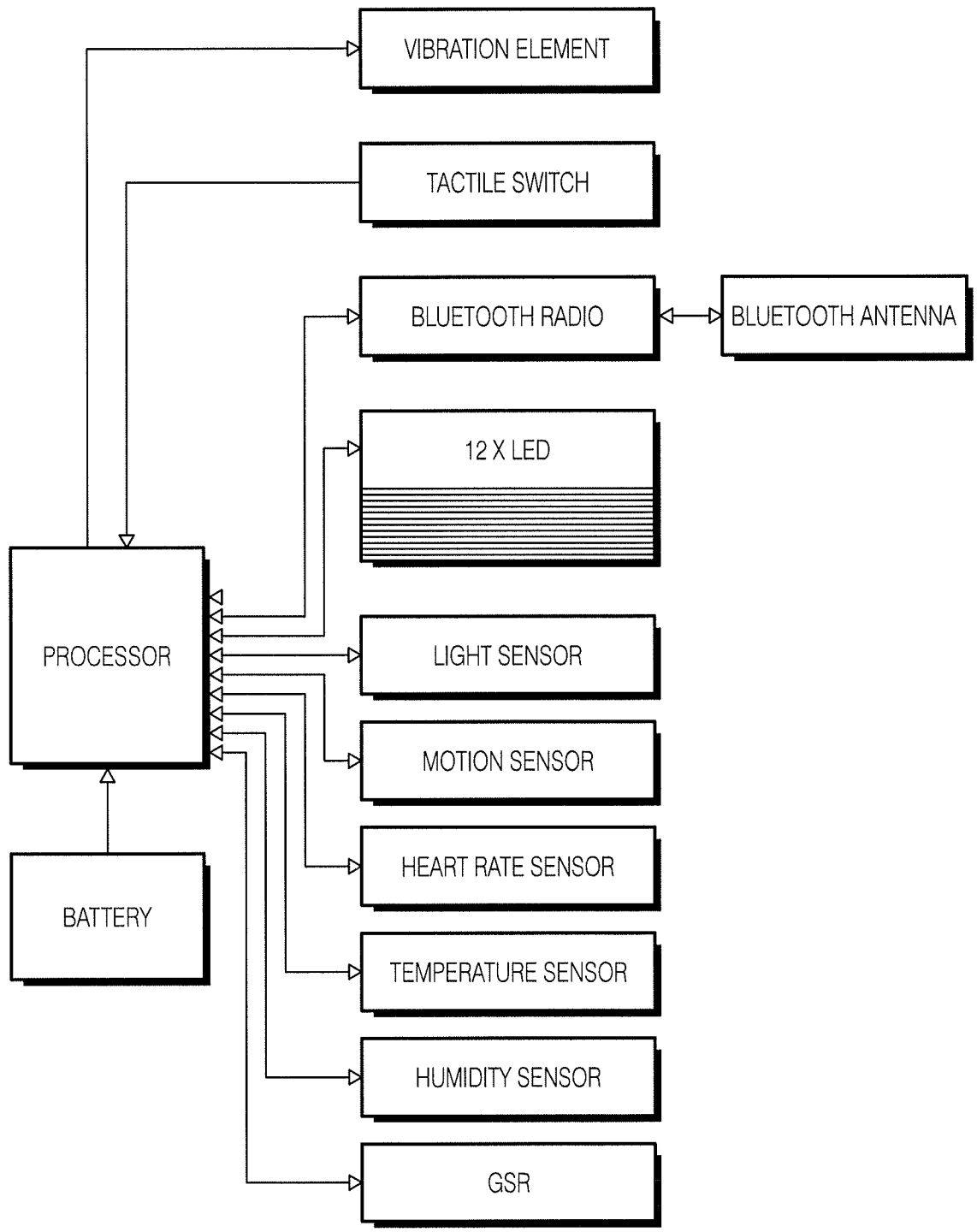
FIG. 3 is a schematic illustration of a craving control device in accordance with some embodiments.

FIG. 3 is a schematic illustration of a craving control device in accordance with some embodiments. The craving control devices can include any and all of the elements illustrated in FIG. 3 and any of the sensors described herein. FIG. 3 illustrates a battery that powers the device. The processor can receive and send signals to the illustrates sensors including the light sensor, motion sensor, heart rate sensor, temperature sensor, humidity sensor, galvanic skin response, or any of the other sensors described herein. The processor can also receive signals from the tactile switch as well as send instructions to the vibration element. The processor can also send and receive signals to any LEDs that are part of the craving control device, such as the 12 LEDs illustrated in FIG. 3. The processor can send and receive data via the Bluetooth radio and Bluetooth antenna. For example, data can be sent from the processor through the Bluetooth radio and antenna wirelessly to a computer network or a device external to the housing of the craving control device. Examples of devices external to the craving control device include: a server, a computer network, a tablet computer, desktop computer, laptop computer, a display, a personal communication device like a smartphone or tablet computer, etc. The processor can send data to a back end server for analysis of the user and information received from the user during the use of the device. The back end server can process the data to learn insights specific to the user and send the processed data to the craving control device and/or a smartphone application. The processed data can modify the psychological and craving support provided by the craving control device and/or the smartphone applications. The examples of sensors illustrated in FIG. 3 are non-limiting as any of the sensors described herein can be included in the craving control devices described herein.

Figure 4:
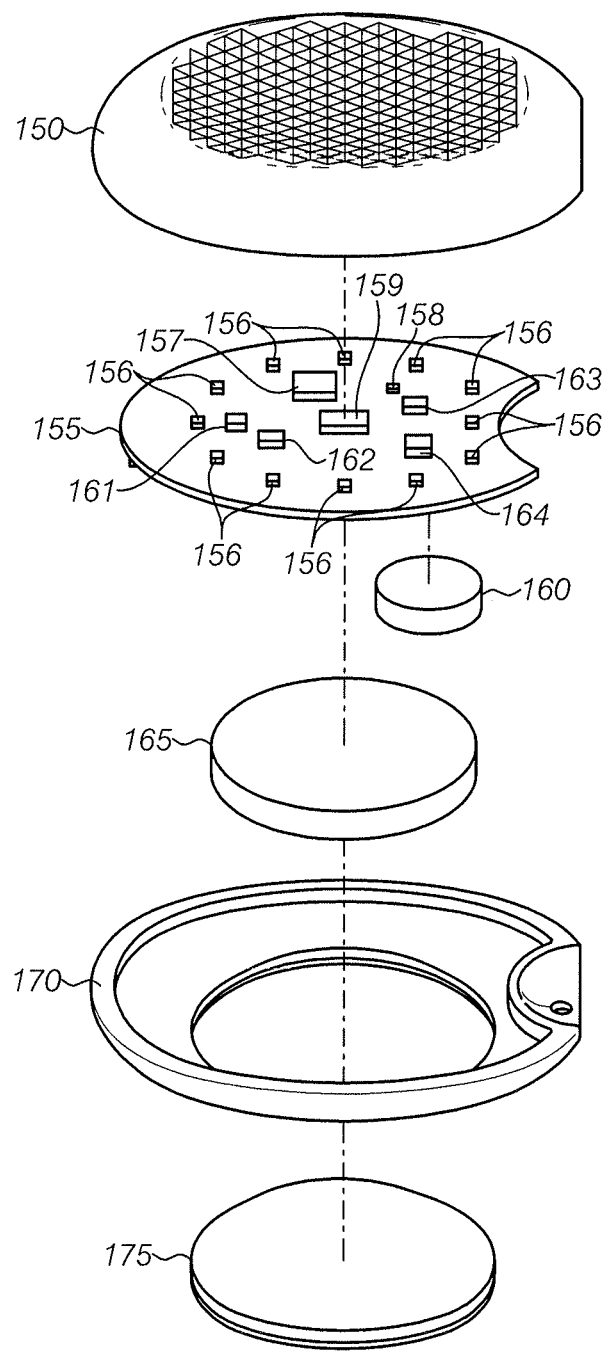
FIG. 4 illustrates an exploded view of a craving control device in accordance with some embodiments.

FIG. 4 illustrates an exploded view of a craving control device 100 in accordance with some embodiments. FIG. 4 illustrates an outer housing surface 150 with the distraction feature (textured area) and the first surface of the housing. A printed circuit board (PCB) 155 is contained within the housing of the craving control device. The PCB 155 can contain or support any and all of the structures illustrated in FIGS. 3. The illustrated PCB 155 includes light sources 156, a processor and radio 157, antenna 158, tactile switch or input actuator 159, environmental sensor 161, first user parameter sensor 162, second user parameter sensor 163, and third user parameter sensor 164. Any of the environmental sensors described herein can be used for the environmental sensor 161. Any of the user parameter sensors described herein can be used for the first user parameter sensor 162, second user parameter sensor 163, and third user parameter sensor 164. The craving control device can include a vibration element 160 that can provide vibration feedback to the user to distract the user during a craving episode. Examples of vibration elements 160 that can be used in the craving control devices described herein include a haptic driver, linear resonance actuators (LRA), eccentric rotating mass (ECM) actuators, and other vibration elements used in electronic devices such as smartphones. In one example, the vibration element is the DRV2605 from Texas Instruments®. The craving control device includes a battery 165 configured to provide power to the components of the craving control device. The craving control device also includes an outer housing surface 170 and a battery door 175. The illustrated outer housing surface 170 includes the second surface of the housing.

Figure 5A:
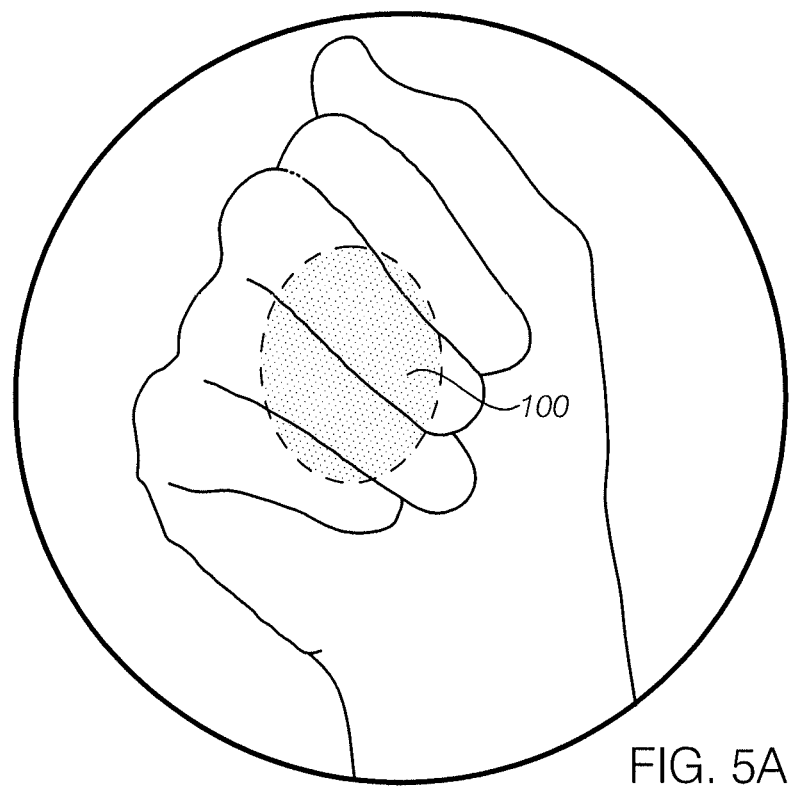
FIG. 5A illustrates an embodiment of a craving control device held in the hand of a user.

FIG. 5A illustrates an embodiment of a craving control device 100 held in the hand of a user. The dimensions and discreet design allow the user to hold the craving control device 100 within their hand such that other people may not notice that they are holding the device. The shape conforms to the palm of the hand and allows user to close a fist around the craving control device.

Figure 5B:
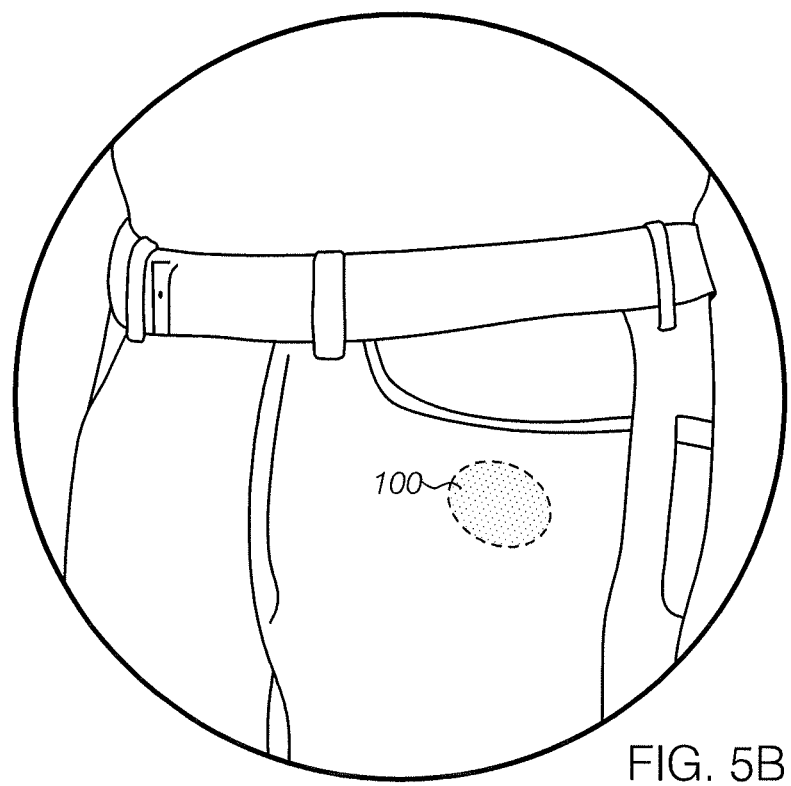
FIG. 5B illustrates an embodiment of a craving control device held in the pocket of a user.

FIG. 5B illustrates an embodiment of a craving control device 100 held in the pocket of a user. The shape and dimensions of the craving control device 100 allow for the user to easily place the craving control deice 100 in the pocket and remove it to use it to provide a craving support, such as by holding the craving control device 100 in the hand as shown in FIG. 5A.

Figure 6A:
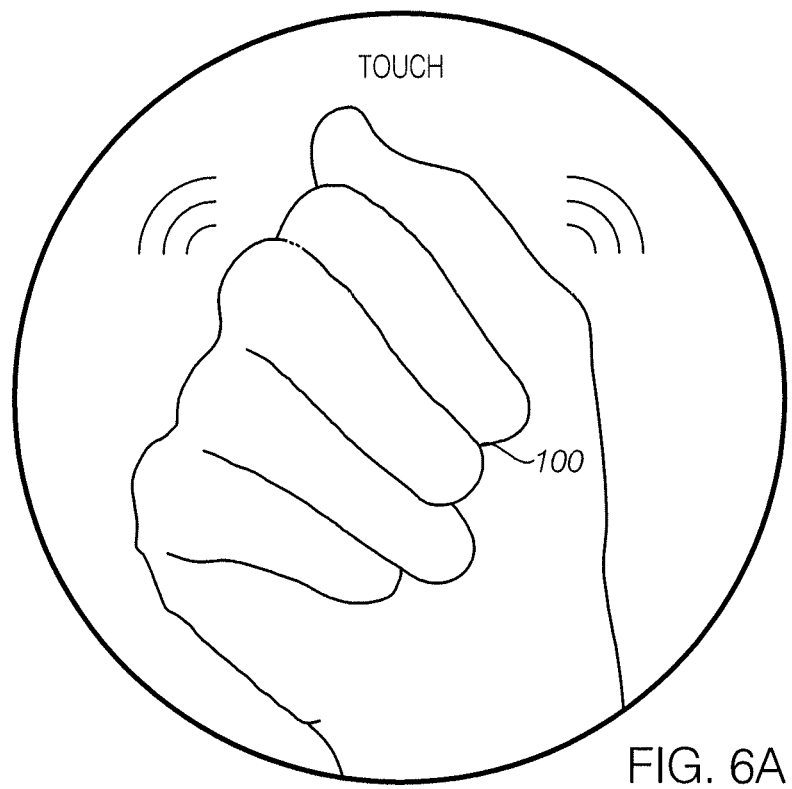
FIG. 6A illustrates an embodiment of a craving control device held in the hand of a user providing touch feedback to the user.

FIG. 6A illustrates an embodiment of a craving control device 100 held in the hand of a user providing touch feedback to the user. Examples of touch feedback that can be provided by the craving control device 100 include haptic feedback that can be provided by a vibration element or other element of the craving control device. The haptic feedback can be provided during part or all of the expected duration of the craving episode. The haptic feedback can be constant, variable, or a repeating pattern.

Figure 6B:
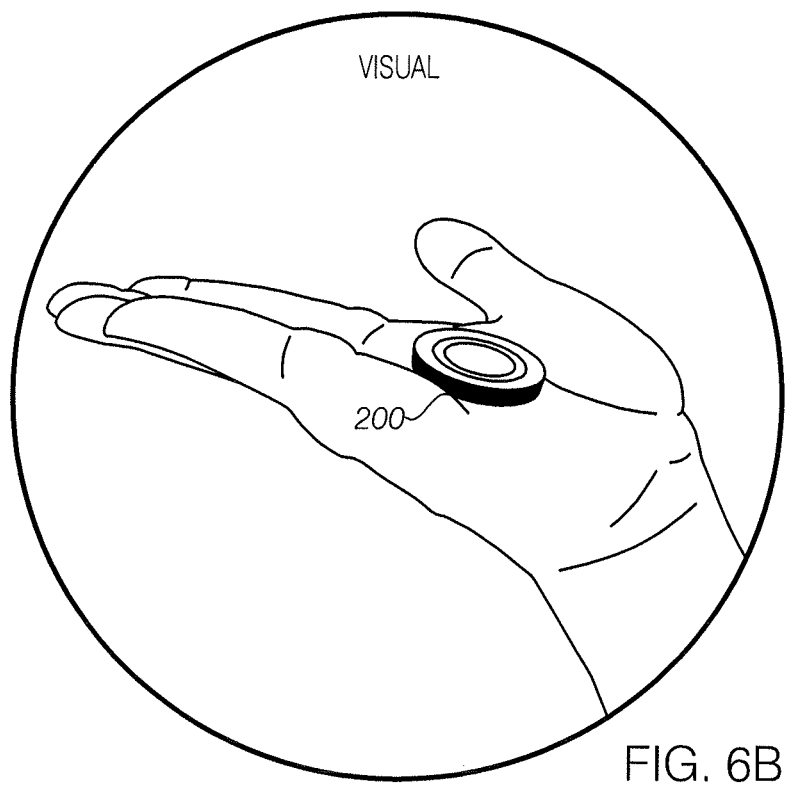
FIG. 6B illustrates an embodiment of a craving control device held in the hand of a user providing visual feedback to the user.

FIG. 6B illustrates an embodiment of a craving control device 200 held in the hand of a user providing visual feedback to the user. The craving control device 200 includes a plurality of LEDs. The visual feedback can be provided by a plurality of light sources, such as LEDs or other visual display.

In some embodiments the craving control device can automatically select the feedback/distraction mode between touch feedback and visual feedback. The sensors on board the craving control device can be used to determine the appropriate feedback modality. For example a light sensor on the craving control device can detect whether the craving control device is in a dark place such as a pocket or a light place such as a hand. When the craving control device detects a dark context, it can use touch feedback (e.g. the haptic-based interface). When the craving control device detects a light environment, it can use visual feedback (e.g. light-based interface). For example, when the craving control device is in a pocket, it can automatically use touch feedback in order to keep the feedback communication discreet. When the craving control device is taken out of a pocket and held in the hand, it can automatically switch to light-based visual feedback so that it can be seen discreetly in the hand. In some embodiments the user can also override the sensor's default behavior via a companion software application, such as software provided on a personal communication device or computer, to select haptic feedback and/or visual feedback when specified conditions are detected by the craving control device.

Figure 7A:
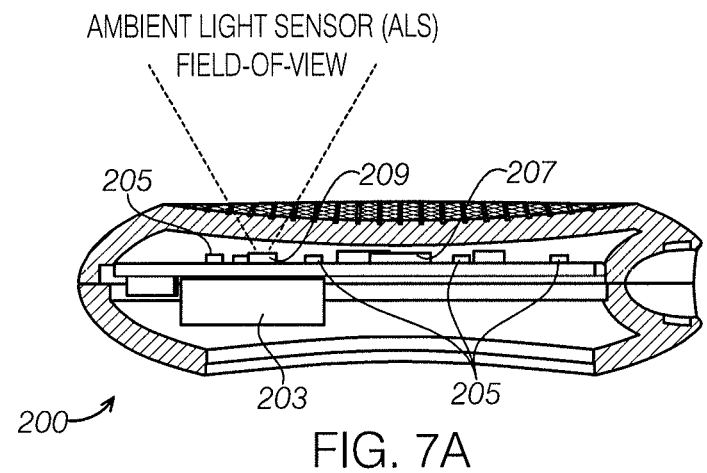
FIG. 7A illustrates a cross-sectional view of an embodiment of a craving control device.
Figure 7B:
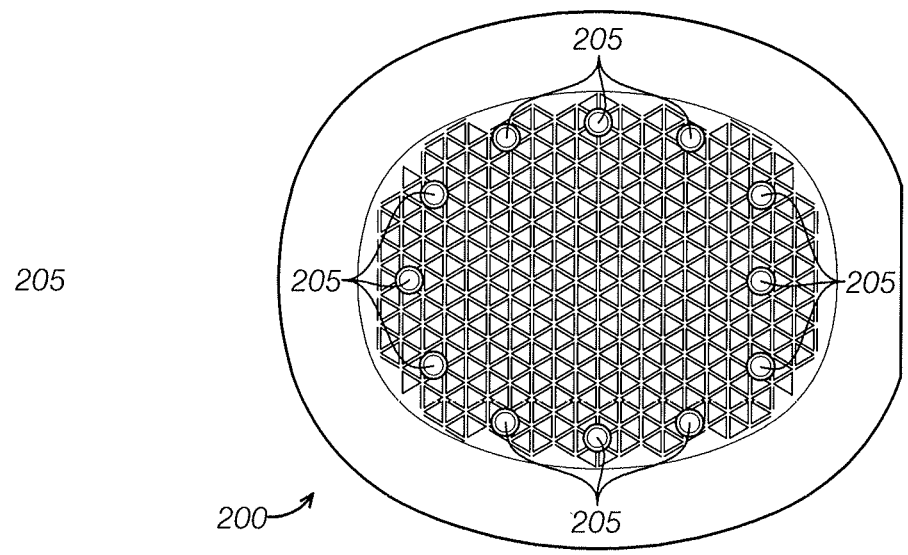
FIG. 7B illustrates a top view of an embodiment of a craving control device.
Figure 7C:
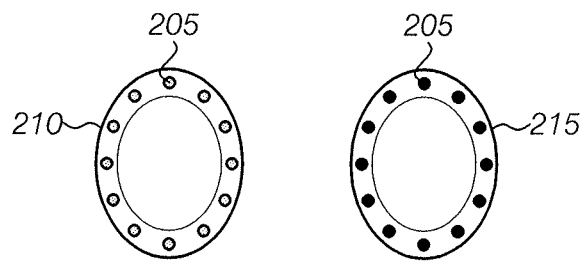
FIG. 7C illustrates two schematics of different light patterns displayed by a craving control device.

FIGS. 7A-7B illustrate an embodiment of a craving control device 200 including a vibration element 203 for touch feedback, light sources 205 for providing visual feedback, a tactile switch or input actuator 207, and an ambient light sensor 209. FIG. 7A also shows an example of a field of view that can be detected by the ambient light sensor 209 within the craving control device 200. The light sources 205 are illustrated as LEDs. FIG. 7B shows the light sources 205 as 12 discrete light sources arranged in a circular pattern. Each of the individual light sources 205 can be separately and individually powered to display a desired pattern to the user. FIG. 7C illustrates a first schematic 210 with the light sources 205 all powered off and a second schematic 215 with all of the light sources 205 powered on.

Figure 8A:
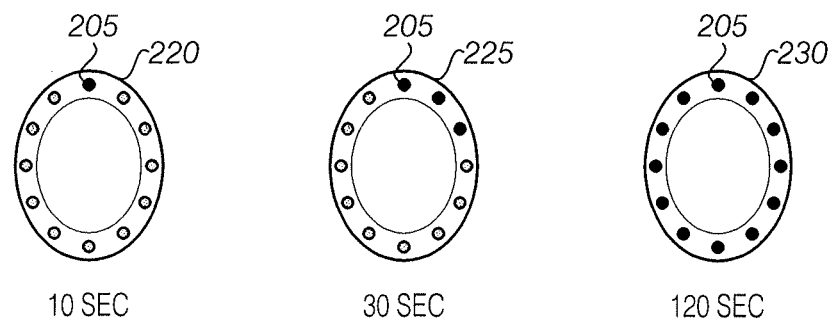
FIG. 8A illustrates three schematics of different light patterns displayed by a craving control device.

FIG. 8A illustrates three schematics (220, 225, 230) of different light patterns displayed by a craving control device 200. The illustrated schematics (220, 225, 230) can function as a timer to provide a countdown to help the individual to allow a craving to pass. The device supports users in allowing cravings to pass by encouraging them to observe the visual or touch feedback and to not give into the craving for a specific amount of time. The timer can be activated upon receiving an input from the user of the craving input actuator of the craving control device. The length of the timer can be selected such that the timer last for an expected duration of a typical craving for the user. The expected duration can be calculated based on user specific craving input data or an average craving episode for a typical user. The timer is communicated via ambient touch or visual feedback depending on the environment. Users can let the timer go through the entire pre-set timer duration (e.g. the illustrated 2 minutes), or they can stop the timer, which then lets the system know that the craving was overcome earlier than the pre-set timer duration. In the illustrated embodiment in FIG. 8A the timer lasts for 120 seconds. In the example illustrated in FIG. 8A the schematic 220 shows one light element 205 lit up to denote 10 seconds. In the example illustrated in FIG. 8A the schematic 225 shows three light elements 205 lit up to denote 30 seconds. In the example illustrated in FIG. 8A the schematic 230 shows twelve light elements 205 lit up to denote 120 seconds. The timer provides craving support to the user by counting down the expected duration of the craving to provide a distraction to the user throughout the expected duration of the craving. Users can also provide input as to whether they overcame the craving using the device or the phone app. In some embodiments the timer duration can be about 180 seconds or less. In some embodiments the timer duration can be about 120 seconds or less. In some embodiments the timer duration can be from about 5 seconds to about 180 seconds.

Figure 8B:
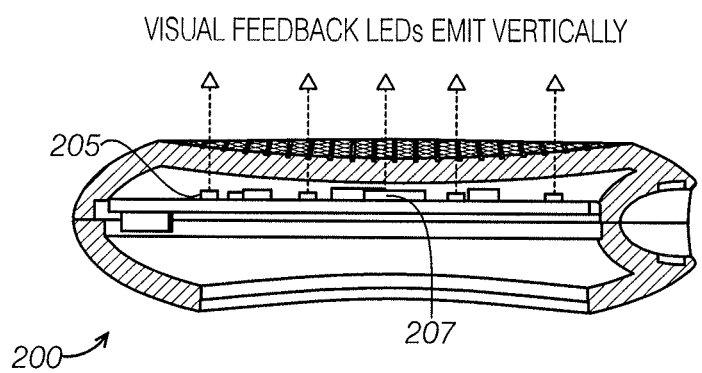
FIG. 8B illustrates a cross-sectional view of an embodiment of a craving control device.

FIG. 8B illustrates a cross-sectional view of an embodiment of a craving control device 200 with an example of the light sources 205 emitting light vertically. The light sources 205 can be configured and mounted to the PCB to emit light vertically through the exterior surface of the housing. This configuration can provide discreet viewing of the light sources to the user while the user holds the device in their hand.

FIG. 9A illustrates a user breathing onto an embodiment of a craving control device 300 adapted to provide a breathing therapy to the user. The craving control device 300 includes the printed circuit board (PCB) 315 shown in FIGS. 9D-9F. The PCB 315 includes a humidity sensor 320, light sources 321, a processor and radio 322, antenna 323, tactile switch or input actuator 324, environmental sensor 325, first user parameter sensor 326, second user parameter sensor 327, and optical heart rate sensor 328. Any of the environmental sensors described herein can be used for the environment sensor 325. Any of the user parameter sensors described herein can be used for the first user parameter sensor 326 and second user parameter sensor 327. The humidity sensor 320 can be used to sense the breathing pattern of the user as shown in FIG. 9A. Other sensors described herein can also be used to sense the breathing pattern of the user, such as the carbon dioxide sensor or a breath sensor. The breathing therapy provided by the craving control device 300 can help calm the user's stress by providing a way to focus on a breathing pattern, which is a common form of stress relief and stress control. Craving support can be provided to reduce stress on the user by focusing the user on the activity of trying to "match" the light patterns displayed on the craving control device 300 to the user's breathing pattern. The breathing therapy can help the user make it through the duration of the craving. The light sources on the craving control device can provide the breathing therapy to the user. FIGS. 9B and 9C illustrate schematics of different light patterns displayed by the craving control device 300. In one schematic example 305 every-other light source or LED pulses on and off soothingly by cross-fading at the same speed in which the user should breathe into the device to match the desired breathing pattern. The user thus attempts to breathe in at the same time the lights are on in example 305. Schematic example 310 shows that as the user sufficiently matches the breathing pattern more of the light sources can go on with each breath until all of the lights turn on indicating that the user has achieved the desired breathing pattern.

Figure 10A:
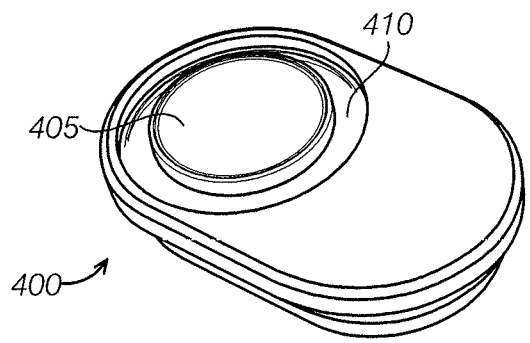
FIG. 10A illustrates an embodiment of a craving control device with a distraction feature.
Figure 10B:
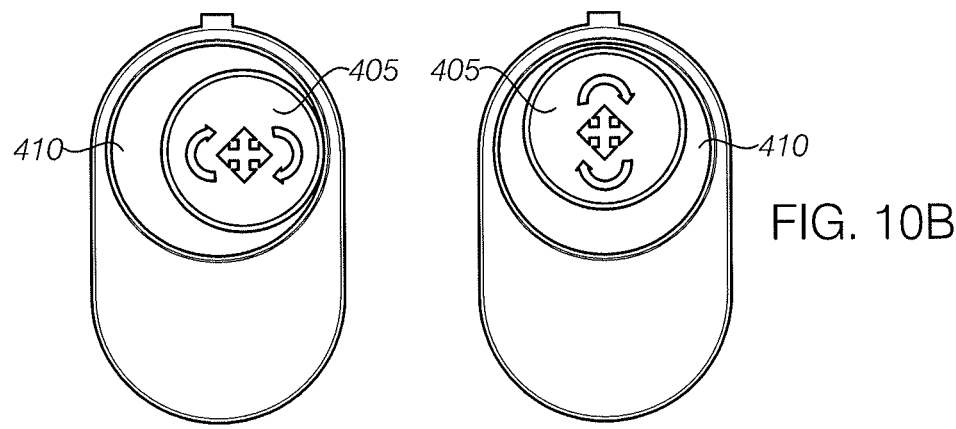
FIG. 10B illustrates an embodiment of a craving control device with a distraction feature at different positions.
Figure 10C:
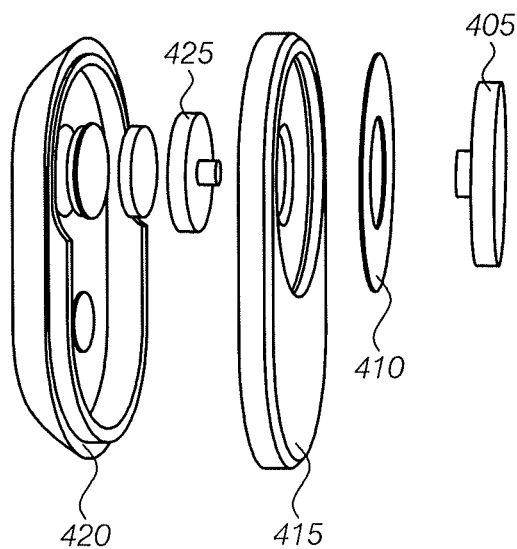
FIG. 10C is an exploded view of an embodiment of a craving control device with a distraction feature.

Quitting an addiction like smoking can also involve redirecting physical habits as in addition to eliminating the dependency on the nicotine drug. In some embodiments the craving control device includes a mechanical feature that allows users to physically play with it to distract from the hand-to-mouth smoking gesture and to give them something to do with their hands. The "fidget" feature or factor can be used as a distraction feature to help the user avoid cravings. FIGS. 10A-10C illustrate a movable mechanical fidget factor and FIGS. 11A-11C illustrate textured mechanical fidget factors in the form of textured surfaces that can contacted or rubbed by the user.

In some embodiments the craving control devices described herein can include a distraction features that is a user-movable element supported by the craving control device housing. The user-movable element can be described as a mechanical fidget factor. FIG. 10A illustrates an embodiment of a craving control device 400 with a distraction feature that is user-movable element 405. The user-movable element 405 can slide relative to a smooth foil 410. FIG. 10B illustrates the user-movable element 405 moved to various positions. FIG. 10C illustrates an exploded view of the craving control device and movable element 405. The craving control device 400 includes a top housing 415 and a bottom housing 420. A disk counter 425 can be engaged with the user-movable element 405 such that it counts or keeps track of the movements of the user-movable element. The disk counter 425 can record user information relating to the craving frequency, craving occurrence, craving intensity, etc. and transfer this information wirelessly to an external device. In some embodiments the user-movable element can also detect a craving based on number of times it is actuated and the frequency. The user-movable element 405 can be incorporated into any of the craving control devices described herein.

FIGS. 11A-11C illustrate multiple different surfaces and textures that can be used in any of the embodiments of craving control devices described herein. The textured or smooth surfaces can be used on the outer surface of the craving control device to allow the users to rub and move their hand on it to help soothe the user during the craving. In the case of smoking cessation treatment the surface also satisfies the user's need to do something with the hands besides hold onto a cigarette. FIG. 11A shows a device with a textured surface 502 in one embodiment of a fidget factor. FIG. 11B shows a device with a smooth surface 504 in one embodiment of a fidget factor. The user can rub the smooth surface similar to the use of a worry stone to provide a soothing treatment. FIG. 11C shows a variety of devices with different surfaces that can be used as a fidget factor such as: raised concentric rings 506, patterns of smooth/matte surface texture combinations 508, 510, a raised surface in a geometric pattern 512, 514 on a concave housing surface, and recessed concentric rings 516.

Figure 12A:
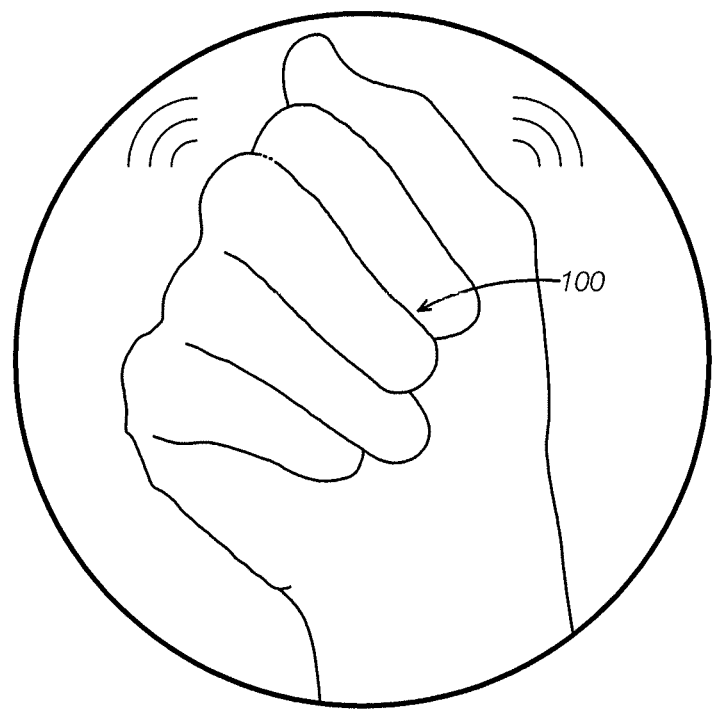
FIG. 12A illustrates an embodiment of a craving control device held in the hand of a user providing a vibrational signal to the user.
Figure 12B:
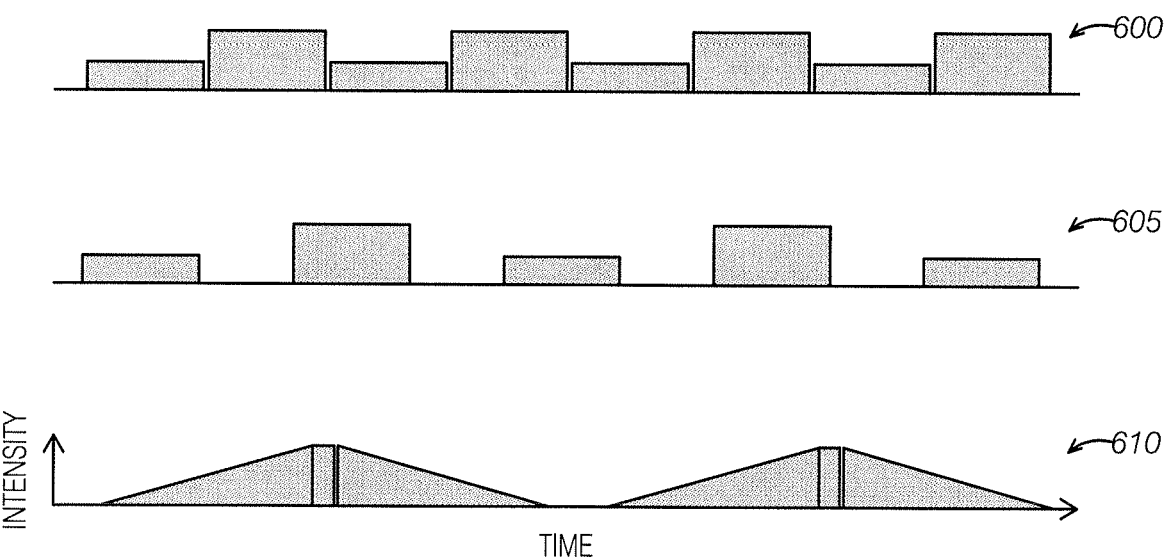
FIG. 12B illustrates examples of vibrational patterns that can be generated by embodiments of the craving control devices and provided to the user.

When the user indicates that they need assistance, the device can provide the user with a soothing pattern that they can use to help manage the brief episode of stress or craving. The pattern can be either pre-defined or programmed by the user. The pattern can be provided by vibrational or haptic feedback. In some embodiments the vibrational feedback can be used to provide a soothing support to the user during the experience of the craving. FIG. 12A illustrates an embodiment of a craving control device 100 held in the hand of a user. The craving control device 100 is providing a vibrational signal to the hand of the user. FIG. 12B illustrates examples of vibrational patterns 600, 605, and 610 that can be provided to the user with time represented by the x-axis and intensity represented by the y-axis. The vibrational pattern 600 illustrates a pattern that alternates a lower intensity vibrational signal with a higher intensity vibrational signal. The vibrational pattern 605 illustrates a repeating pattern that provides a lower intensity vibrational signal, a pause with no vibrational signal, and a higher intensity vibrational signal. The vibrational pattern can be preselected or tailored to an expected duration of the craving, e.g. 120 seconds. In some embodiments the vibrational pattern can be random. In some embodiments the vibrational pattern can be selected by the user or determined based on user information or user inputs to the craving control device regarding the timing, frequency, and intensity of the cravings.

The user can record the severity and mood of a craving based on press pattern of the craving input actuator. A software algorithm can be used to calculate the severity of the craving based on frequency and duration of presses over a duration of time. For example, if the button is pressed multiple times in a short amount of time (seconds) or, alternatively, if the button is pressed firmly vs. gently, then the system detects that craving as being more severe. The level of severity of the craving can be visualized in the cravings graphed in a companion app running on a mobile device or pc (see FIG. 24 for an example). FIG. 13A illustrates a top view of an embodiment of a craving control device 700 with a textured surface 705 that can be pressed or tapped by the user to actuate a craving input actuator. FIG. 13B illustrates a chart showing an embodiment correlating button taps to craving intensity. In the example shown in FIG. 13B if a single button press is recorded then the intensity of the craving can be recorded as neutral or a default intensity. In the example shown in FIG. 13B if multiple taps are recorded, such as 2-4 button presses, and the duration between button presses is greater than a predetermined amount like 300 ms then the intensity of the craving can be recorded as having an elevated intensity. In the example shown in FIG. 13B if multiple taps above a predetermined number, such as more than 4 button presses, and/or the duration between button presses is less than a predetermined amount like 150 ms then the intensity of the craving can be recorded as having a high intensity. Other thresholds can be used to classify the intensity of the cravings. For example the duration, number of button presses, and intensity correlation can be developed uniquely for the user based on past user information relating to the user's craving and/or addiction type. FIG. 13C illustrates a cross-sectional view the craving control device 700 showing the vibration component 710, tactile switch or craving input actuator 715, and user parameter sensor or environmental sensor 720. The button press of the craving input actuator 715 and information sensor can be used in combination with the user parameter sensor or environmental sensor 720 to determine information relating to the craving timing, frequency, and/or intensity. Any of the user parameter sensors or environmental sensors described herein can be used for the user parameter sensor or environmental sensor 720. Examples of user parameter sensors that can be used include humidity sensor, breath sensor, nicotine sensor, carbon monoxide sensor, carbon dioxide sensor, oxygen sensor, inertia sensor, electrocardiogram (ECG) lead, electromyography (EMG) lead, accelerometer, blood pressure sensor, galvanic skin response sensor, temperature sensor, and heart rate sensor, Examples of environmental sensors that can be used include an ambient light sensor, ultraviolet light sensor, air pressure sensor, environmental pollutant sensor, and a temperature sensor.

Figure 14A:
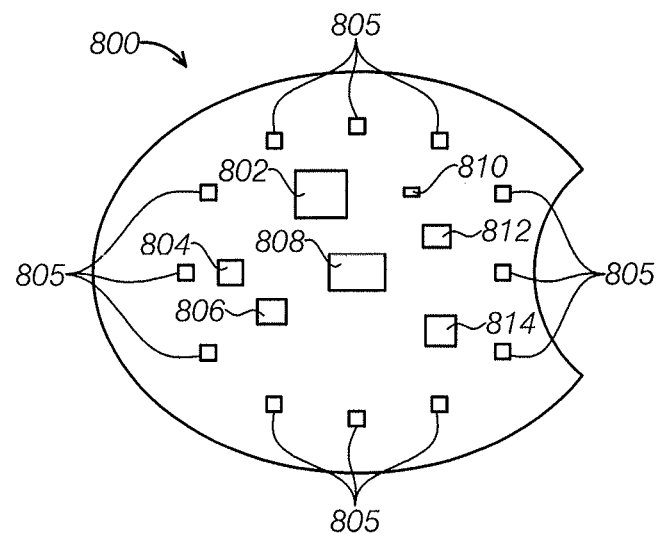
FIG. 14A illustrates a top view of an embodiment of a printed circuit board with sensors that can be used in the craving control devices described herein.
Figure 14B:
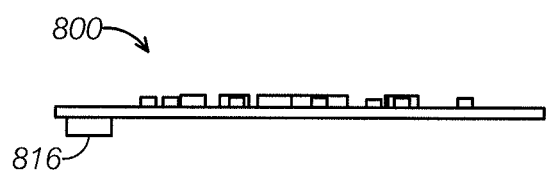
FIG. 14B illustrates a side view of an embodiment of a printed circuit board with sensors that can be used in the craving control devices described herein.
Figure 14C:
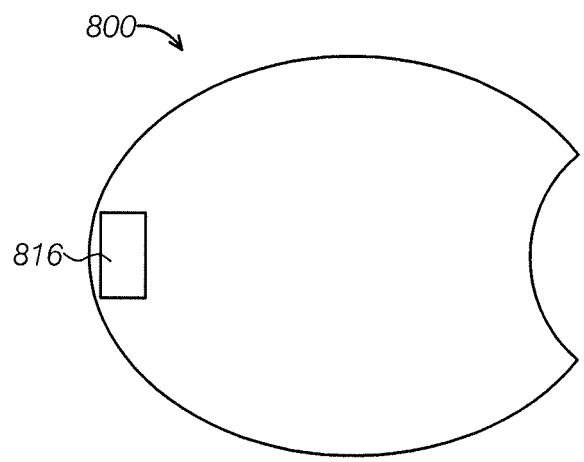
FIG. 14C illustrates a bottom view of an embodiment of a printed circuit board with sensors that can be used in the craving control devices described herein.

FIGS. 14A, 14B, and 14C illustrate a top view, side view, and bottom view of a printed circuit board (PCB) 800 with hardware and sensors that can be used in the craving control devices described herein. The illustrated PCB 800 includes a processor and radio 802, ambient light sensor 804, light sources 805, temperature and humidity sensor 806, tactile switch or input actuator 808, inertial measurement unit (IMU) 814, galvanic skin response (GSR) sensor 812, antenna 810, and optical heart rate sensor 816. The PCB 800 can also include additional user parameter sensors and environmental sensors. Examples of user parameter sensors that can be used include humidity sensor, breath sensor, nicotine sensor, carbon monoxide sensor, carbon dioxide sensor, oxygen sensor, inertia sensor, electrocardiogram (ECG) lead, electromyography (EMG) lead, accelerometer, blood pressure sensor, galvanic skin response sensor, temperature sensor, and heart rate sensor. Examples of environmental sensors that can be used include an ambient light sensor, ultraviolet light sensor, air pressure sensor, environmental pollutant sensor, and a temperature sensor.

Figure 15:
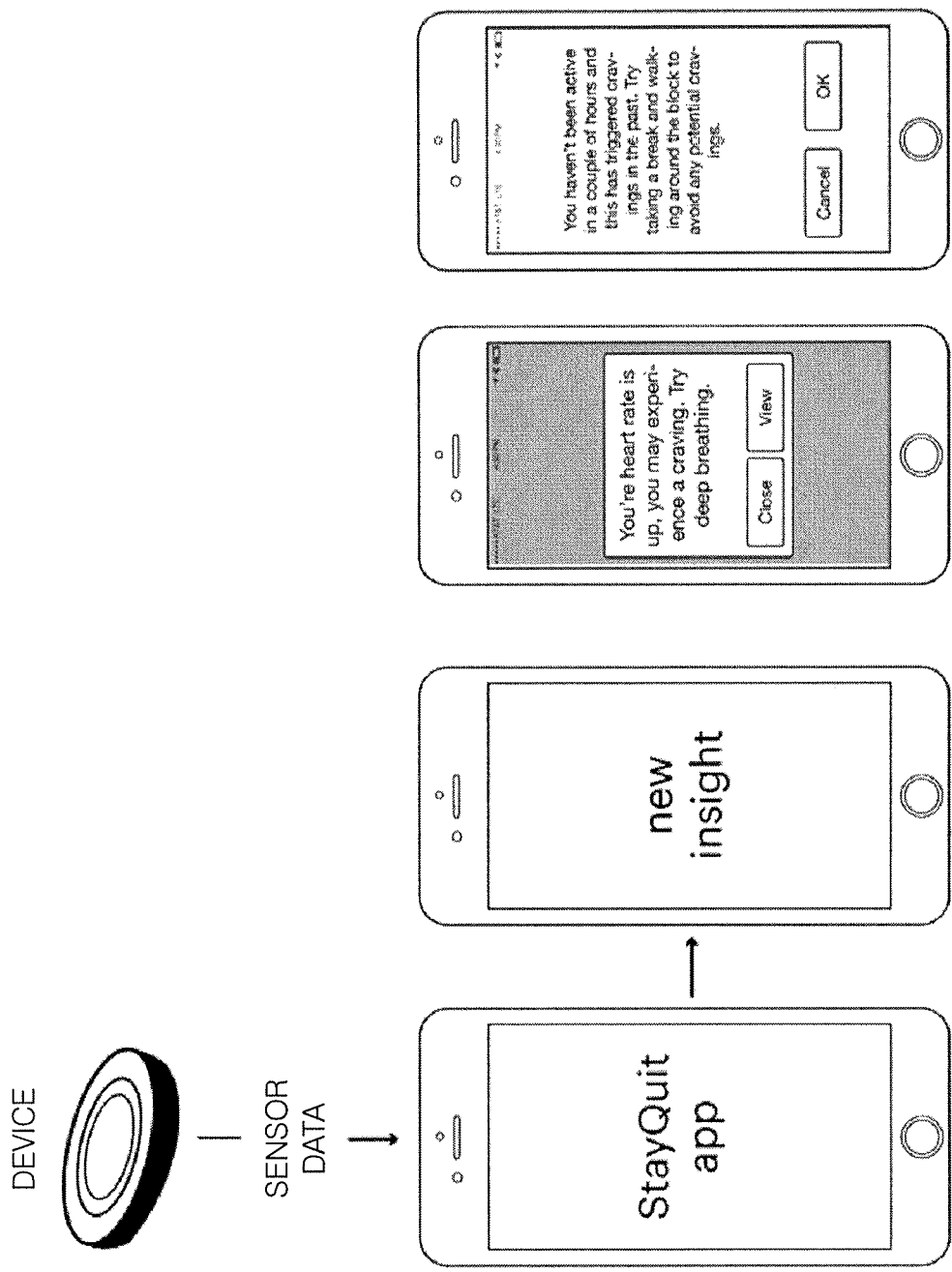
FIG. 15 illustrates a schematic example of a craving control device interfacing with a personal communication device along with samples for images displayed by the personal communication device in accordance with some embodiments.
Figure 16:
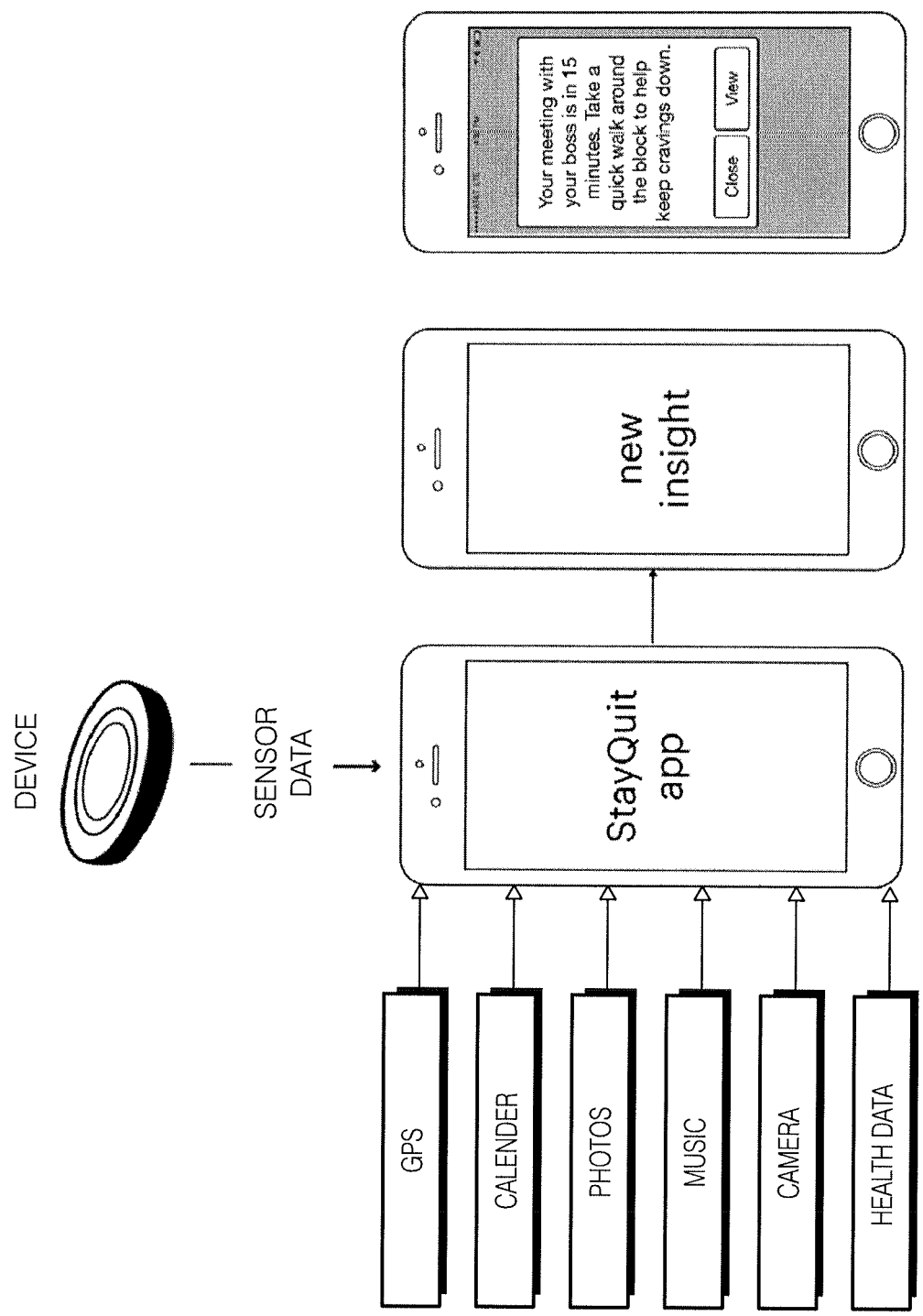
FIG. 16 illustrates a schematic example of a craving control device interfacing with user data and a personal communication device along with samples for images displayed by the personal communication device in accordance with some embodiments.
Figure 24:
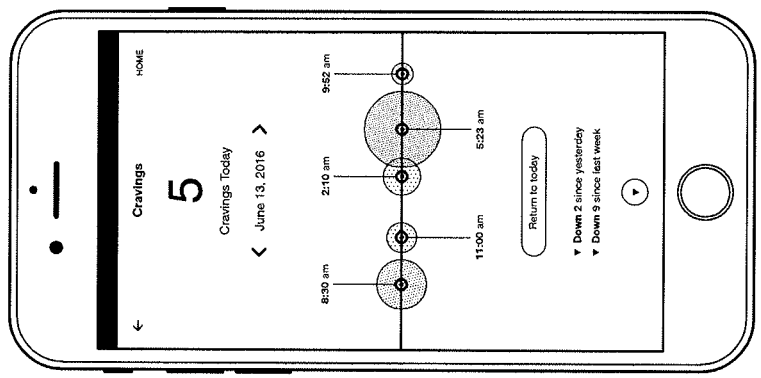
FIG. 24 illustrates a schematic example of a craving control device interfacing with user data and a personal communication device along with samples for images displayed by the personal communication device in accordance with some embodiments.
Figure 24:
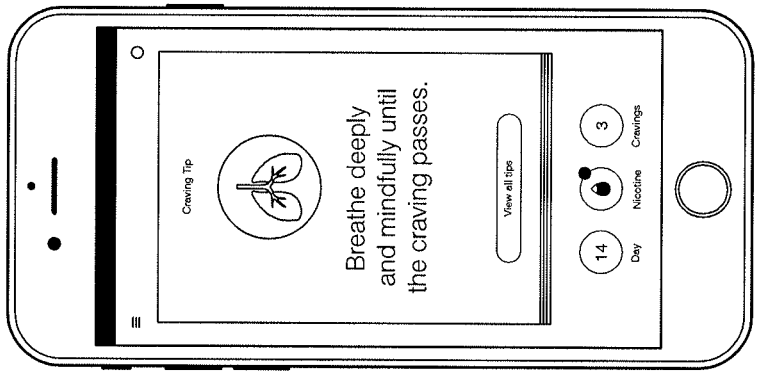

The craving control devices can send and receive data to a personal communication device running a companion application to the craving control device. The companion application can provide information, insights, craving support, messages, and notices to the user. FIGS. 15, 16, and 24 illustrate a schematic example of a craving control device interfacing with a personal communication device along with samples for images displayed by the personal communication device in accordance with some embodiments.

FIG. 15 illustrates a craving control device sending sensor data to the smartphone and companion application. The sensor data can be from any of the sensors described herein, including the user parameter sensors and environmental parameter sensors. The sensor data/information can then be applied to the real-time coaching on the companion smartphone application that is used to customize the information, guidance and/or suggested actions provided to the user. For example, the device can sense a user's elevated heart rate and then, via the companion app, guide the user through a deep breathing or meditation exercise to lower the heart rate and calm down. In another example, a spike in the reading of the galvanic skin response sensor plus data from the accelerometer can determine if the user has a heightened emotional state without moving (e.g. eliminating sneezing, laughing or exercising) which is applied to the mood and emotional state recorded with the craving. The smartphone application can generate a new insight for the user. The smartphone application can also provide a notification to the user. FIG. 15 illustrates the smartphone application providing a notification to the user that "You're heart rate is up, you may experience a craving. Try deep breathing." FIG. 15 illustrates the smartphone providing a notification that "You haven't been active in a couple of hours and this has triggered cravings in the past. Try taking a break and walking around the block to avoid any potential cravings."

In some embodiments the companion smartphone application can receive and analyze data from a source other than the craving control device. For example, the companion smartphone application can use $3^{rd}$ party data in combination with data from the craving control device. For example, in addition to collecting biometric data via sensors on the craving control device, the companion smartphone application can hook into $3^{rd}$ party data and services that can be used in combination to create even more personal insights based on new correlations identified between the different sets of data. Examples of $3^{rd}$ party data and services include GPS to detect location and Calendar to detect context of what users are doing at a given time. The information is used to determine patterns in times of heightened cravings such as stressful meetings at work or at the bar with friends. FIG. 16 illustrates an example of the smartphone companion application receiving sensor data from the craving control device and $3^{rd}$ party data. The $3^{rd}$ party data illustrated in FIG. 16 includes GPS, calendar, photos, music, camera, and/or health data. The $3^{rd}$ party data can be harvested from the user's smartphone, e-mail, other smartphone applications, or other sources. The illustrated smartphone application screens use calendar data to provide the following notice to the user "Your meeting with your boss is in 15 minutes. Take a quick walk around the block to help keep cravings down.

FIG. 24 illustrates additional examples of information that can be provided by the craving control device and companion smartphone application. The user records a craving by pushing the button on the craving control device to actuate the craving input actuator. The data is sent to the smartphone and companion smartphone application. The left image displayed on the smartphone is a diagram showing real-time coaching that can be displayed as a result of the cravings and severity of cravings that are recorded. The more severe, the more urgent the suggestion. The illustrated image provides a message to the user to breathe deeply until the craving passes. The right image displayed on the smartphone illustrates a diagram representing the number of cravings a user has recorded that day. In the illustrated visualization, the user can see the severity that they recorded based on how many times they pushed the craving control device button and the frequency in which they pressed it. FIG. 24 also illustrates displaying the severity of the craving by assigning a larger circle size for the visualization of the craving to indicate a more intense craving. The visualization illustrated in FIG. 24 represents 1 day; however the user can navigate through the days of the program and also see a weekly view of the timeline or other desired time period.

Figure 17:
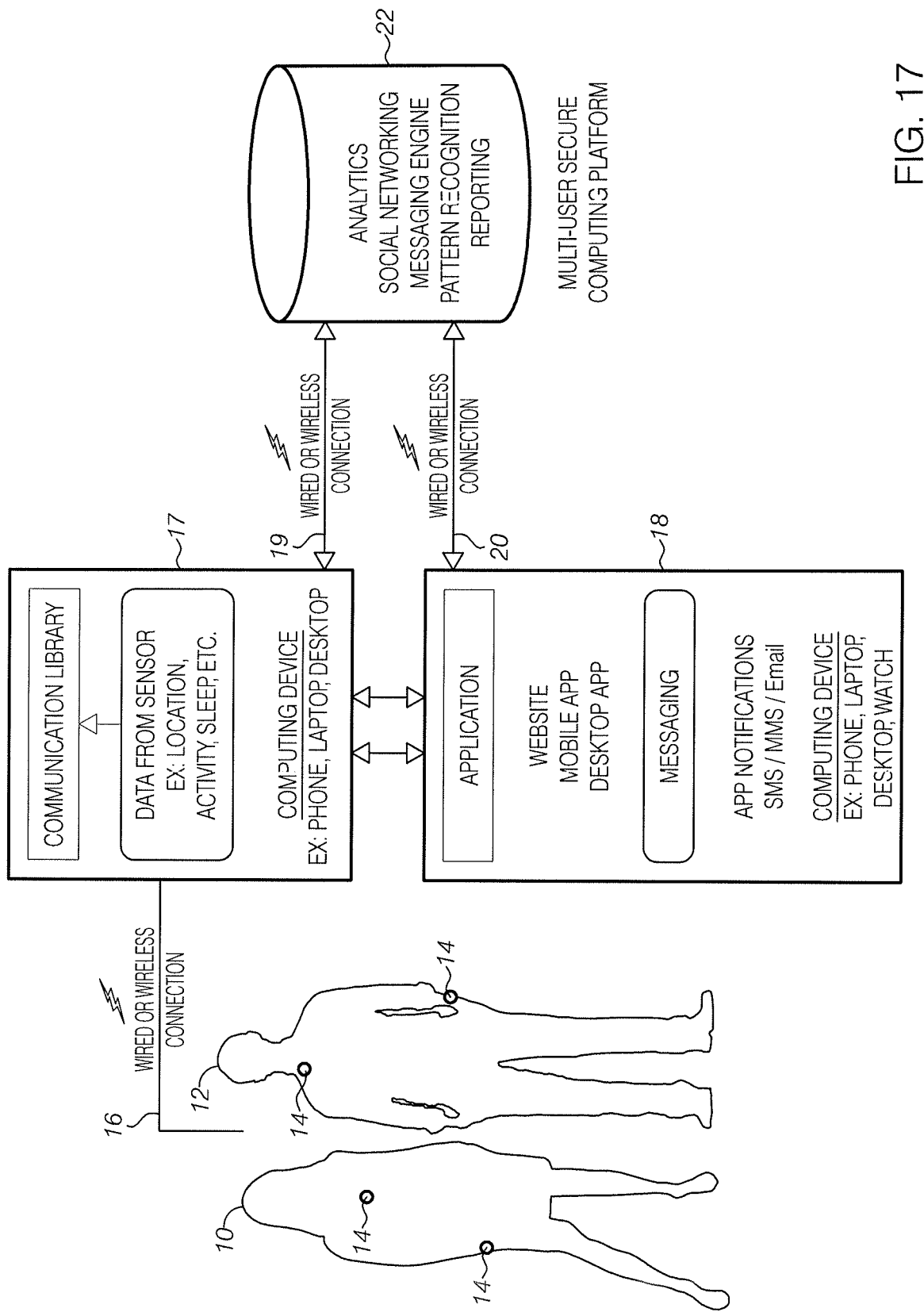
FIG. 17 shows one embodiment of a craving input mechanism and a network environment for interfacing with it.

FIG. 17 shows one embodiment of a craving input mechanism and a network environment for interfacing with it. To show the many different ways the craving input mechanism can be worn, FIG. 17 shows two users 10 and 12 each wearing a craving input mechanism 14 in two locations. User 10 has a first craving input mechanism 14 in a pocket and second craving input mechanism 14 hanging as a necklace from the user's neck. User 12 is wearing a first craving input mechanism 14 as a bracelet on the user's wrist and a second craving input mechanism 14 pinned or otherwise support on a shirt collar. (In normal use, each user requires only one craving input mechanism.) Each user can discretely actuate the craving input mechanism 14 to send information about a craving episode (including any information gathered by a sensor in the craving input mechanism 14 providing information about, e.g., location, activity, sleep, etc.) over a wired or wireless connection 16 to a first computing device 17 (e.g., a smartphone) having a communication library. In some embodiments, the first computing device 17 has sensors that collect additional or duplicative data (e.g., activity data, location data, date and/or time, etc.) that can be compared to, and correlated with, data coming from the craving input mechanism 14. In some embodiments, first computing device 17 may communicate with a second computing device 18 configured to integrate data from other sources to which it has access (e.g., telephone logs, web sites visited, etc.) which can be correlated with data collected elsewhere (such as from first computer 17 or from a remote server). Applications running on second computing device 18 may also be configured to provide additional functionality, such as algorithmic prompts or messaging (SMS/MMS, email, or other notifications). The computing devices 17 and 18 may also communicate over wired or wireless connections 19 and 20 with a secure multi-user computing platform 22 providing analytics, social networking, messaging, pattern recognition and/or reporting.

Figure 18A:
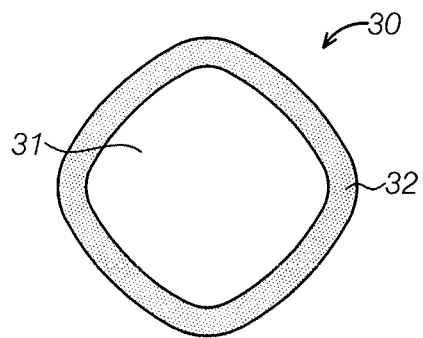
FIGS. 18A and 18B show top and cross-sectional views of an embodiment of a craving input mechanism.
Figure 19A:
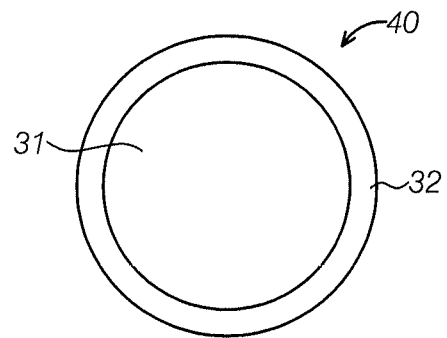
FIGS. 19A and 19B show top and cross-sectional views of an embodiment of a craving input mechanism.
Figure 18B:
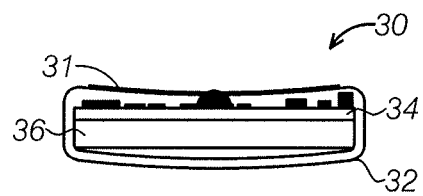
Figure 19B:
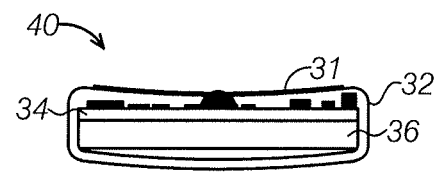
Figure 20A:
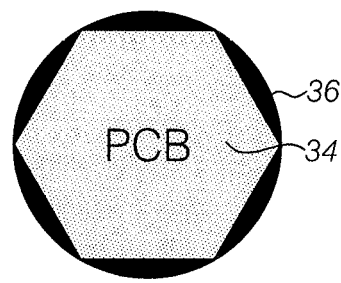
FIGS. 20A and 20B are top and cross-sectional views of the printed circuit board and battery for use with a mechanism in accordance with some embodiments.
Figure 20B:

FIGS. 18A and 18B show top and cross-sectional views of an embodiment of a craving input mechanism 30 having a diamond shape. FIGS. 19A and 19B show top and cross-sectional views of an embodiment of a craving input mechanism 40 having a round shape. Both embodiments have a housing 32 enclosing a printed circuit board 34 (with a CPU, Bluetooth LE components, input component (e.g., tactile switch, capacitive touch, accelerometer) and memory and a battery 36). A port or door for replacing the battery 36 may be provided on the underside of the mechanism 30 or mechanism 40. Depressing a button 31 on the top of each of mechanism 30 and mechanism 40 actuates the Bluetooth communication components to identify a craving input by the user. FIGS. 20A and 20B are top and cross-sectional views of the printed circuit board 34 and battery 36 for use with mechanism 30 or mechanism 40.

Figure 21:
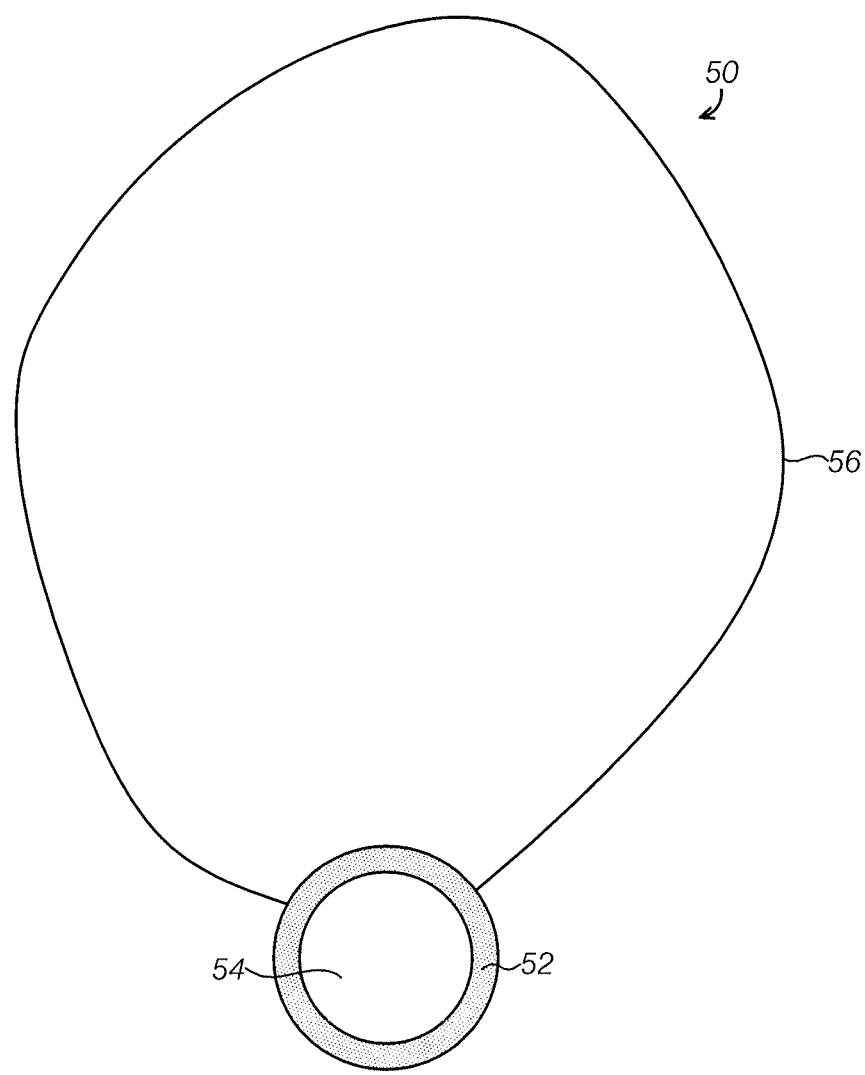
FIG. 21 shows a craving input mechanism with a button in a housing or support structure supported by a necklace chain in accordance with some embodiments.

The basic craving input mechanism shown in FIGS. 18 and 19 may be combined with different housings, support structure and attachment mechanisms to meet a user's needs. For example, FIG. 21 shows a craving input mechanism 50 with a button 52 in a housing or support structure 54 supported by a necklace chain 56. A user can wear craving input mechanism 50 and discretely activate 52 in the event of a craving episode.

Figure 22:
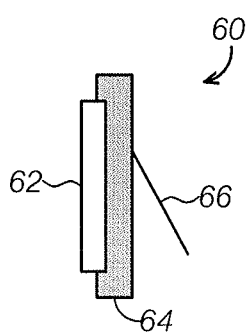
FIG. 22 shows a craving input mechanism with a button in a housing or support from which an attachment pin extends in accordance with some embodiments.

FIG. 22 shows a craving input mechanism 60 with a button 62 in a housing or support 64 from which an attachment pin 66 extends. Pin 66 may be used to attach craving input mechanism 60 to the user's clothing.

Figure 23:
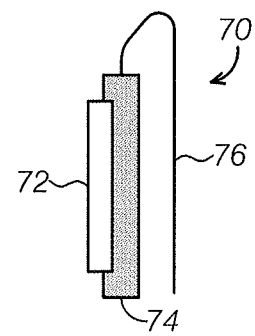
FIG. 23 shows a craving input mechanism with a button in a housing or support from which a clip extends in accordance with some embodiments.

FIG. 23 shows a craving input mechanism 70 with a button 72 in a housing or support 74 from which a clip 76 extends. Clip 76 may be used to attach craving input mechanism 70 to a user's collar, shoe or other clothing or article surface.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A craving control device comprising:
   a housing,
   a craving input actuator supported by the housing, the craving input actuator being configured to obtain information from a user pertaining to a timing, frequency, or intensity of a craving,
   a wireless communicator supported by the housing,
   a controller operatively connected to the craving input actuator and the wireless communicator to communicate craving timing, frequency, or intensity information received by the craving input actuator via the wireless communicator to a device external to the housing, and a distraction feature comprising a timer adapted to distract the user during a craving episode, the time comprising a vibration source operable by the controller to vibrate for the expected duration of the craving episode.

2. The craving control device of claim 1, wherein the housing is sized and configured to be enclosed in the user's hand.

3. The craving control device of claim 1, wherein the housing is sized and configured to be placed in a pocket of the user's clothing.

4. The craving control device of claim 1, wherein the housing is sized and configured to be worn on the user's clothing.

5. The craving control device of claim 1, wherein the timer starts with actuation of the craving input actuator.

6. The craving control device of claim 1, wherein the timer comprises a visual display configured to change during the expected duration of the craving episode.

7. The craving control device of claim 6, wherein the visual display comprises a plurality of lights.

8. The craving control device of claim 1, wherein the controller is configured to operate the vibration source to vibrate with an intensity that varies during the expected duration of the craving episode.

9. The craving control device of claim 1, further comprising a user parameter sensor supported by the housing and adapted to obtain user parameter information relevant to the craving, the controller being operatively connected to the user parameter sensor to communicate user parameter information sensed by the sensor via the wireless communicator to the device external to the housing.

10. The craving control device of claim 1, further comprising an environmental parameter sensor supported by the housing and adapted to obtain environmental information relevant to the craving, the controller being operatively connected to the environmental parameter sensor to communicate environmental parameter information sensed by the sensor via the wireless communicator to the device external to the housing.

11. A craving control device comprising:
a housing,
a craving input actuator supported by the housing, the craving input actuator being configured to obtain information from a user pertaining to a timing, frequency, or intensity of a craving,
a wireless communicator supported by the housing,
a controller operatively connected to the craving input actuator and the wireless communicator to communicate craving timing, frequency, or intensity information received by the craving input actuator via the wireless communicator to a device external to the housing, and
a breath sensor and a display supported by the housing, the controller being operatively connected to the display to provide a target breathing pattern for the user and to the breath sensor to measure a breathing pattern of the user.

12. The craving control device of claim 1, further comprising the external device, wherein the external device comprises a personal communication device having a processor programmed to electronically send a message to a support contact provided by the user.

13. The craving control device of claim 1, further comprising the external device, wherein the external device comprises a personal communication device having a processor programmed to provide craving support to the user in response to craving information from the craving input actuator.

14. The craving control device of claim 13, the processor further programmed to provide the craving support proactively to the user based on a past information from the user pertaining to craving occurrence and craving intensity.

15. The craving control device of claim 13, wherein the craving control device further comprises a user parameter sensor, the personal communication device processor being further programmed to provide craving support to the user in response to a user parameter sensed by the sensor.

16. The craving control device of claim 9, wherein the user parameter sensor comprises one or more of a: humidity sensor, breath sensor, nicotine sensor, carbon monoxide sensor, carbon dioxide sensor, oxygen sensor, inertia sensor, electrocardiogram (ECG) lead, electromyography (EMG) lead, accelerometer, blood pressure sensor, galvanic skin response sensor, temperature sensor, and heart rate sensor.

17. The craving control device of claim 14, wherein the craving control device further comprises an environmental parameter sensor, the personal communication device processor being further programmed to provide craving support to the user in response to environmental parameter information sensed by the sensor.

18. The craving control device of claim 10, wherein the environmental parameter sensor comprises an ambient light sensor, ultraviolet light sensor, air pressure sensor, environmental pollutant sensor, or a temperature sensor.

19. The craving control device of claim 1, wherein the controller is further configured to determine the intensity of the craving based on a pattern received by the input actuator.

20. A method of receiving a craving input from a user comprising:
receiving information from the user pertaining to a craving occurrence and an intensity of a craving with a craving control device comprising a housing and a craving input actuator supported by the housing, the information from the user pertaining to the craving occurrence and craving intensity of the craving received through the craving input actuator;
wirelessly communicating craving occurrence and craving intensity information received by the craving input actuator to a device external to the housing; and
providing a distraction to the user in response to the craving occurrence and craving intensity information with a distraction feature that is part of the craving control device by starting a timer marking an expected duration of the craving episode after actuation of the craving input actuator, the timer comprising a vibration source operable by the controller, and vibrating the vibration source for the expected duration of the craving episode.

21. The method of claim 20, further comprising providing a visual display with the timer that changes during the expected duration of the craving episode.

22. The method of claim 21, wherein providing the visual display comprises providing a plurality of lights.

23. The method of claim 20, further comprising varying an intensity of the vibration source during the expected duration of the craving episode.

24. The method of claim 20, further comprising receiving a user parameter information relevant to the craving with a user parameter sensor supported by the housing and wirelessly transmitting data corresponding to the user parameter information to the device external to the housing.

25. The method of claim 20, further comprising receiving an environmental parameter information relevant to the craving with an environmental parameter sensor supported by the housing and wirelessly transmitting data corresponding to the environmental parameter information to the device external to the housing.

26. A method of receiving a craving input from a user comprising:
receiving information from the user pertaining to a craving occurrence and an intensity of a craving with a craving control device comprising a housing and a craving input actuator supported by the housing, the information from the user pertaining to the craving occurrence and craving intensity of the craving received through the craving input actuator;
wirelessly communicating craving occurrence and craving intensity information received by the craving input actuator to a device external to the housing; and
receiving breathing parameter information relevant to the craving from the user with a breath sensor supported by the housing and providing a target breathing pattern for the user with a display supported by the housing or with a display of the external device.

27. The method of claim 20, further comprising providing a craving support to the user in response to craving information from the craving input actuator with the external device.

28. The method of claim 27, further comprising receiving information from a user parameter sensor supported by the housing and providing a craving support to the user based on a user parameter sensed by the user parameter sensor.

29. The method of claim 28, wherein the user parameter sensor comprises one or more of a: humidity sensor, breath sensor, nicotine sensor, carbon monoxide sensor, carbon dioxide sensor, oxygen sensor, inertia sensor, electrocardiogram (ECG) lead, electromyography (EMG) lead, accelerometer, blood pressure sensor, galvanic skin response sensor, temperature sensor, and heart rate sensor.

30. The method of claim 27, further comprising receiving information from an environmental parameter sensor supported by the housing and providing a craving support to the user based on the environmental parameter sensed by the environmental parameter sensor.

31. The method of claim 30, wherein the environmental parameter sensor comprises an ambient light sensor, ultraviolet light sensor, air pressure sensor, environmental pollutant sensor, or a temperature sensor.

32. The method of claim 20, wherein the housing is sized and configured to be enclosed in the user's hand.

33. The method of claim 20, wherein the housing is sized and configured to be placed in a pocket of the user's clothing.

34. The method of claim 20, wherein the external device comprises a personal communication device comprising a display and further comprising providing information to the user with the display of the personal communication device relating to the timing and intensity of the cravings.

35. The method of claim 20, further comprising determining the intensity of the craving based on a pattern received by the input actuator.

36. The method of claim 20, wherein the external device comprises a personal communication device and further comprising electronically sending a message to a support contact provided by the user upon receiving information from the user pertaining to the occurrence and intensity of the craving.

37. The method of claim 20, further comprising providing a distraction to the user proactively based on a past information from the user pertaining to craving occurrence and craving intensity.

* * * * *